United States Patent
Giliyar et al.

(10) Patent No.: US 9,034,858 B2
(45) Date of Patent: May 19, 2015

(54) HIGH-STRENGTH TESTOSTERONE UNDECANOATE COMPOSITIONS

(75) Inventors: Chandrashekar Giliyar, Salt Lake City, UT (US); Basawaraj Chickmath, Salt Lake City, UT (US); Chidambaram Nachiappan, Sandy, UT (US); Mahesh V. Patel, Salt Lake City, UT (US); Srinivansan Venkateshwaran, Salt Lake City, UT (US)

(73) Assignee: Lipocine Inc., Salt Lake City, UT (US)

(*) Notice: Subject to any disclaimer, the term of this patent is extended or adjusted under 35 U.S.C. 154(b) by 0 days.

(21) Appl. No.: 13/485,807

(22) Filed: May 31, 2012

(65) Prior Publication Data

US 2012/0244215 A1    Sep. 27, 2012

Related U.S. Application Data

(63) Continuation-in-part of application No. 12/957,206, filed on Nov. 30, 2010, and a continuation-in-part of application No. PCT/US2011/062538, filed on Nov. 30, 2011.

(51) Int. Cl.
| | |
|---|---|
| *A61P 15/08* | (2006.01) |
| *A61K 9/48* | (2006.01) |
| *A61K 31/568* | (2006.01) |

(52) U.S. Cl.
CPC ............ *A61K 31/568* (2013.01); *A61K 9/4875* (2013.01)

(58) Field of Classification Search
CPC ......................... A61K 9/4875; A61K 31/568
USPC ........................................................ 514/178
See application file for complete search history.

(56) References Cited

U.S. PATENT DOCUMENTS

| | | | |
|---|---|---|---|
| 2,680,749 A | 6/1954 | Cawley et al. | |
| 2,742,487 A | 4/1956 | Robledano | |
| 3,097,139 A | 7/1963 | Thorp | |
| 3,097,144 A | 7/1963 | Banker | |
| 3,164,520 A | 1/1965 | Huber | |
| 3,266,991 A | 8/1966 | Wettstein et al. | |
| 3,510,561 A | 5/1970 | Koh | |
| 4,098,802 A | 7/1978 | van der Vies | |
| 4,147,783 A | 4/1979 | Van der Vies | |
| 4,156,719 A | 5/1979 | Sezaki et al. | |
| 4,177,188 A | 12/1979 | Hansen et al. | |
| 4,196,188 A | 4/1980 | Besins | |
| 4,220,599 A * | 9/1980 | van der Vies | 552/638 |
| 4,239,754 A | 12/1980 | Sache et al. | |
| 4,388,307 A | 6/1983 | Cavanak | |
| 4,439,432 A | 3/1984 | Peat | |
| 4,572,915 A | 2/1986 | Crooks | |
| 4,579,730 A | 4/1986 | Kidron et al. | |
| 4,628,052 A | 12/1986 | Peat | |
| 4,628,098 A | 12/1986 | Nohara et al. | |
| 4,654,327 A | 3/1987 | Teng | |
| 4,656,161 A | 4/1987 | Herr | |
| 4,689,333 A | 8/1987 | Nohara et al. | |
| 4,695,450 A | 9/1987 | Bauer | |
| 4,703,042 A | 10/1987 | Bodor | |
| 4,713,246 A | 12/1987 | Begum et al. | |
| 4,717,569 A | 1/1988 | Harrison et al. | |
| 4,717,596 A | 1/1988 | Barbee et al. | |
| 4,719,239 A | 1/1988 | Muller et al. | |
| 4,727,109 A | 2/1988 | Schmidt et al. | |
| 4,731,384 A | 3/1988 | Dell | |
| 4,795,327 A | 1/1989 | Gaylord et al. | |
| 4,832,952 A | 5/1989 | Hersh et al. | |
| 4,834,965 A | 5/1989 | Martani et al. | |
| 4,849,227 A | 7/1989 | Cho | |
| 4,867,984 A | 9/1989 | Patel | |
| 4,874,795 A | 10/1989 | Yesair | |
| 4,880,634 A | 11/1989 | Speiser | |
| 4,895,726 A | 1/1990 | Curtet et al. | |

(Continued)

FOREIGN PATENT DOCUMENTS

| | | |
|---|---|---|
| DE | 10108614 | 9/2002 |
| EP | 0036145 | 5/1985 |

(Continued)

OTHER PUBLICATIONS

Seidman, et al.; "Testosterone replacement therapy for hypogonadal men with SSRI-refractory depression"; Journal of Affective Disorders 48 (1998) 157-161.
Sefton, "Implantable pumps," Crit. Rev. Biomed. Eng. 14(3): pp. 201-240 (1987) (Abstract).
Shanghai Pi Chemicals Ltd. "Material Safety Data Sheet: Testosterone Undecanoate," Online 2007, retrieved Jun. 3, 2009 from http://www.pipharm.com/products/msds/msds-13457.pdf.
Stedman's Medical Dictionary (28th Ed), 2006, "Surfactants", Lippincott Williams & Wilkins Co.
Stedman's Medical Dictionary (28th Ed), 2006, "steroid", "Dehydro-e-epiandrosterone", and "Dehydroisoandrosterone" Lippincott Williams & Wilkins Co.
Tauber, U. et al., "Absolute bioavailability of testosterone after oral administration of testosterone-undecanoate and testosterone," Eur. J. Drug Metab. Pharmacokinetics 11(2): pp. 145-149 (1986) (Abstract).
Wilson, C.G. and O'Mahony, B., "The Behaviour of Fats and Oils in the Upper G.I. Tract," Bulletin Technique Gattefosse 90: pp. 13-18 (1997).

(Continued)

*Primary Examiner* — Mina Haghighatian
(74) *Attorney, Agent, or Firm* — Thorpe North & Western, LLP

(57) ABSTRACT

The present disclosure is drawn to pharmaceutical compositions and oral dosage capsules containing testosterone undecanoate, as well as related methods. The capsule includes a capsule shell and a capsule fill. The capsule fill can include a solubilizer and about 14 wt % to about 35 wt % testosterone undecanoate based on the total capsule fill. The oral dosage capsule is such that when a single oral administration to a male subject of one or more capsules with a total testosterone undecanoate daily dose of about 350 mg to about 650 mg it provides a ratio of serum testosterone $C_{max}$ to serum testosterone $C_{ave}$ of about 2.7 or less. In yet another embodiment, a method for providing a serum concentration of testosterone within a target serum testosterone concentration $C_{ave}$ range for a male subject is provided.

27 Claims, No Drawings

(56) References Cited

U.S. PATENT DOCUMENTS

| | | |
|---|---|---|
| 4,897,269 A | 1/1990 | Mezei |
| 4,900,734 A | 2/1990 | Maxson et al. |
| 4,925,672 A | 5/1990 | Gremm |
| 4,944,949 A | 7/1990 | Story |
| 4,961,890 A | 10/1990 | Boyer |
| 4,963,540 A | 10/1990 | Maxson et al. |
| 4,994,439 A | 2/1991 | Longenecker et al. |
| 5,023,108 A | 6/1991 | Bageria et al. |
| 5,026,560 A | 6/1991 | Makino et al. |
| 5,035,891 A | 7/1991 | Runkel et al. |
| 5,045,321 A | 9/1991 | Makino et al. |
| 5,057,319 A | 10/1991 | Gottwald et al. |
| 5,071,643 A | 12/1991 | Yu et al. |
| 5,091,187 A | 2/1992 | Haynes |
| 5,091,188 A | 2/1992 | Haynes |
| 5,093,132 A | 3/1992 | Makino et al. |
| 5,104,656 A | 4/1992 | Seth et al. |
| 5,120,710 A | 6/1992 | Liedtke |
| 5,140,021 A | 8/1992 | Maxon et al. |
| 5,145,684 A | 9/1992 | Liversidge |
| 5,152,997 A | 10/1992 | Ebert et al. |
| 5,206,219 A | 4/1993 | Desai |
| 5,244,925 A | 9/1993 | Wretlind |
| 5,252,339 A | 10/1993 | Cristofori et al. |
| 5,270,005 A | 12/1993 | Raible |
| 5,270,055 A | 12/1993 | Moest |
| 5,300,529 A | 4/1994 | Narayanan |
| 5,340,589 A | 8/1994 | Stetsko et al. |
| 5,342,625 A | 8/1994 | Hauer et al. |
| 5,350,741 A | 9/1994 | Takada |
| 5,364,632 A | 11/1994 | Benita et al. |
| 5,374,446 A | 12/1994 | Ferenz et al. |
| 5,376,688 A | 12/1994 | Morton et al. |
| 5,380,535 A | 1/1995 | Geyer et al. |
| 5,384,133 A | 1/1995 | Boyes et al. |
| 5,389,382 A | 2/1995 | List |
| 5,403,593 A | 4/1995 | Royce |
| 5,433,959 A | 7/1995 | Makino et al. |
| 5,444,041 A | 8/1995 | Owen |
| 5,500,224 A | 3/1996 | Vranckx et al. |
| 5,532,002 A | 7/1996 | Story |
| 5,539,000 A | 7/1996 | Leonard |
| 5,543,393 A | 8/1996 | Kim et al. |
| 5,545,628 A | 8/1996 | Deboeck et al. |
| 5,560,931 A | 10/1996 | Eickhoff et al. |
| 5,571,533 A | 11/1996 | Santus et al. |
| 5,571,536 A | 11/1996 | Eickhoff et al. |
| 5,573,783 A | 11/1996 | Desieno et al. |
| 5,589,455 A | 12/1996 | Woo |
| 5,589,513 A | 12/1996 | Magyar et al. |
| 5,593,971 A | 1/1997 | Tschollar et al. |
| 5,614,491 A | 3/1997 | Walch et al. |
| 5,616,330 A | 4/1997 | Kaufman et al. |
| 5,622,721 A | 4/1997 | Dansereau et al. |
| 5,624,687 A | 4/1997 | Yano et al. |
| 5,626,869 A | 5/1997 | Nyqvist et al. |
| 5,629,021 A | 5/1997 | Wright |
| 5,633,015 A | 5/1997 | Gillis et al. |
| 5,633,226 A | 5/1997 | Owen |
| 5,635,520 A | 6/1997 | Uda |
| 5,639,474 A | 6/1997 | Woo |
| 5,639,478 A | 6/1997 | Makino et al. |
| 5,639,724 A | 6/1997 | Cavanak |
| 5,645,856 A | 7/1997 | Lacy et al. |
| 5,646,109 A | 7/1997 | Owen et al. |
| 5,653,987 A | 8/1997 | Modi et al. |
| 5,656,277 A | 8/1997 | Berlati et al. |
| 5,656,289 A | 8/1997 | Cho et al. |
| 5,665,379 A | 9/1997 | Herslof et al. |
| 5,681,584 A | 10/1997 | Savastano et al. |
| 5,686,105 A | 11/1997 | Kelm et al. |
| 5,688,761 A | 11/1997 | Owen et al. |
| 5,698,155 A | 12/1997 | Grosswald et al. |
| 5,707,648 A | 1/1998 | Yiv |
| 5,714,477 A | 2/1998 | Einarsson |
| 5,726,181 A | 3/1998 | Hausheer et al. |
| 5,731,355 A | 3/1998 | Jones et al. |
| 5,736,161 A | 4/1998 | Garces et al. |
| 5,741,512 A | 4/1998 | Hauer et al. |
| 5,741,822 A | 4/1998 | Yesair |
| 5,747,066 A | 5/1998 | Pittrof et al. |
| 5,756,450 A | 5/1998 | Hahn et al. |
| 5,759,997 A | 6/1998 | Cavanak |
| 5,766,629 A | 6/1998 | Cho et al. |
| 5,767,069 A | 6/1998 | Ko et al. |
| 5,776,495 A | 7/1998 | Duclos et al. |
| 5,795,883 A | 8/1998 | Hesch et al. |
| 5,798,333 A | 8/1998 | Sherman |
| 5,811,120 A | 9/1998 | Gibson et al. |
| 5,817,320 A | 10/1998 | Stone |
| 5,827,536 A | 10/1998 | Laruelle |
| 5,846,971 A | 12/1998 | Sangekar et al. |
| 5,853,748 A | 12/1998 | New |
| 5,855,905 A | 1/1999 | Oettel et al. |
| 5,858,398 A | 1/1999 | Cho |
| 5,858,401 A | 1/1999 | Bhalani et al. |
| 5,866,159 A | 2/1999 | Hauer et al. |
| 5,874,418 A | 2/1999 | Stella et al. |
| 5,880,148 A | 3/1999 | Edgar et al. |
| 5,883,109 A | 3/1999 | Gregg et al. |
| 5,891,469 A | 4/1999 | Amselem |
| 5,891,845 A | 4/1999 | Myers |
| 5,916,589 A | 6/1999 | Hauer et al. |
| 5,922,355 A | 7/1999 | Parikh et al. |
| 5,948,773 A | 9/1999 | Akiyama et al. |
| 5,948,825 A | 9/1999 | Takahashi et al. |
| 5,962,014 A | 10/1999 | Hauer et al. |
| 5,962,017 A | 10/1999 | Hauer et al. |
| 5,965,161 A | 10/1999 | Oshlack et al. |
| 5,976,574 A | 11/1999 | Gordon |
| 5,981,479 A | 11/1999 | Ko et al. |
| 5,981,586 A | 11/1999 | Pershadsingh |
| 5,989,583 A | 11/1999 | Amselem |
| 5,993,880 A | 11/1999 | Frost et al. |
| 6,007,840 A | 12/1999 | Hauer et al. |
| 6,008,192 A | 12/1999 | Al-Razzak et al. |
| 6,013,665 A | 1/2000 | DeMichele et al. |
| 6,017,560 A | 1/2000 | Makino et al. |
| 6,022,852 A | 2/2000 | Klokkers et al. |
| 6,024,978 A | 2/2000 | Hauer et al. |
| 6,027,747 A | 2/2000 | Terracol et al. |
| 6,042,847 A | 3/2000 | Kerc et al. |
| 6,046,177 A | 4/2000 | Stella et al. |
| 6,057,339 A | 5/2000 | Gregg |
| 6,066,653 A | 5/2000 | Gregg et al. |
| 6,074,670 A | 6/2000 | Stamme et al. |
| 6,086,376 A | 7/2000 | Moussa et al. |
| 6,096,338 A | 8/2000 | Lacy et al. |
| 6,123,962 A | 9/2000 | Makino et al. |
| 6,160,007 A | 12/2000 | DeMichele et al. |
| 6,174,547 B1 | 1/2001 | Dong et al. |
| 6,180,138 B1 | 1/2001 | Engh et al. |
| 6,189,486 B1 | 2/2001 | Lindholm |
| 6,193,985 B1 | 2/2001 | Sonne |
| 6,221,395 B1 | 4/2001 | Maggi et al. |
| 6,224,840 B1 | 5/2001 | Kim et al. |
| 6,228,399 B1 | 5/2001 | Parikh et al. |
| 6,228,400 B1 | 5/2001 | Lee et al. |
| 6,248,363 B1 | 6/2001 | Patel et al. |
| 6,255,100 B1 | 7/2001 | Ko et al. |
| 6,267,985 B1 | 7/2001 | Chen et al. |
| 6,287,594 B1 | 9/2001 | Wilson |
| 6,294,192 B1 | 9/2001 | Patel et al. |
| 6,296,876 B1 | 10/2001 | Odidi et al. |
| 6,299,904 B1 | 10/2001 | Shimizu et al. |
| 6,303,662 B1 | 10/2001 | Nagahama et al. |
| 6,306,825 B1 | 10/2001 | Cavanak |
| 6,309,663 B1 | 10/2001 | Patel et al. |
| 6,328,993 B1 | 12/2001 | Linder et al. |
| 6,328,994 B1 | 12/2001 | Shimizu et al. |
| 6,340,471 B1 | 1/2002 | Kershman et al. |
| 6,342,246 B2 | 1/2002 | Johnson et al. |
| 6,361,796 B1 | 3/2002 | Rudnic et al. |
| 6,368,634 B1 | 4/2002 | Remon |

(56) References Cited

U.S. PATENT DOCUMENTS

| | | |
|---|---|---|
| 6,379,705 B1 | 4/2002 | Mendes et al. |
| 6,383,471 B1 | 5/2002 | Chen et al. |
| 6,383,510 B1 | 5/2002 | Linder et al. |
| 6,383,517 B1 | 5/2002 | Qiu et al. |
| 6,391,342 B1 | 5/2002 | Henriksen et al. |
| 6,432,445 B1 | 8/2002 | Ambuhl et al. |
| 6,444,225 B1 | 9/2002 | Sherman |
| 6,447,806 B1 | 9/2002 | Gassmann et al. |
| 6,451,339 B2 | 9/2002 | Patel et al. |
| 6,455,518 B2 | 9/2002 | Zenke et al. |
| 6,458,373 B1 | 10/2002 | Lambert et al. |
| 6,458,383 B2 | 10/2002 | Chen et al. |
| 6,465,016 B2 | 10/2002 | Parikh et al. |
| 6,468,559 B1 | 10/2002 | Chen et al. |
| 6,475,519 B1 | 11/2002 | Minzer et al. |
| 6,503,894 B1 | 1/2003 | Dudley et al. |
| 6,531,139 B1 | 3/2003 | Gao et al. |
| 6,569,463 B2 | 5/2003 | Patel et al. |
| 6,589,552 B2 | 7/2003 | Stamm et al. |
| 6,589,562 B1 | 7/2003 | Shefer et al. |
| 6,623,755 B2 | 9/2003 | Chen et al. |
| 6,630,134 B1 | 10/2003 | Klein |
| 6,652,880 B1 | 11/2003 | Aylwin et al. |
| 6,660,286 B1 | 12/2003 | Lambert et al. |
| 6,665,880 B2 | 12/2003 | Poppe |
| 6,667,048 B1 | 12/2003 | Lambert et al. |
| 6,692,766 B1 | 2/2004 | Rubinstein et al. |
| 6,696,482 B2 | 2/2004 | Shenoy et al. |
| 6,720,001 B2 | 4/2004 | Chen et al. |
| 6,737,082 B1 | 5/2004 | Darder |
| 6,761,903 B2 | 7/2004 | Chen et al. |
| 6,881,745 B2 | 4/2005 | Hayes et al. |
| 6,887,493 B2 | 5/2005 | Shefer et al. |
| 6,913,244 B1 | 7/2005 | Atkinson et al. |
| 6,923,988 B2 | 8/2005 | Patel et al. |
| 6,977,083 B1 | 12/2005 | Huebler et al. |
| 6,982,281 B1 | 1/2006 | Chen et al. |
| 7,025,979 B2 | 4/2006 | Nieschlag et al. |
| 7,374,779 B2 | 5/2008 | Chen et al. |
| 7,658,944 B2 | 2/2010 | Holm et al. |
| 7,718,640 B2 | 5/2010 | Hubler et al. |
| 8,241,664 B2 | 8/2012 | Dudley et al. |
| 8,338,395 B2 | 12/2012 | Hubler et al. |
| 8,778,922 B2 | 7/2014 | Giliyar et al. |
| 2001/0018069 A1 | 8/2001 | Johnson et al. |
| 2002/0006443 A1 | 1/2002 | Curatolo et al. |
| 2002/0013304 A1 | 1/2002 | Wilson et al. |
| 2002/0058066 A1 | 5/2002 | Tomohira et al. |
| 2002/0068693 A1 | 6/2002 | Jeng et al. |
| 2002/0102301 A1 | 8/2002 | Schwarz |
| 2002/0103139 A1 | 8/2002 | Weisspapir et al. |
| 2002/0183296 A1 | 12/2002 | Dudley et al. |
| 2003/0022875 A1 | 1/2003 | Wilson et al. |
| 2003/0072798 A1 | 4/2003 | Schwarz et al. |
| 2003/0077297 A1 | 4/2003 | Chen et al. |
| 2003/0082215 A1 | 5/2003 | Lemut et al. |
| 2003/0104048 A1 | 6/2003 | Patel et al. |
| 2003/0180352 A1 | 9/2003 | Patel et al. |
| 2003/0181431 A1 | 9/2003 | Hodgen |
| 2003/0186892 A1 | 10/2003 | Taneja |
| 2003/0228358 A1 | 12/2003 | Perlman et al. |
| 2003/0235595 A1 | 12/2003 | Chen et al. |
| 2003/0236236 A1 | 12/2003 | Chen et al. |
| 2004/0002445 A1 | 1/2004 | Taneja |
| 2004/0048896 A1 | 3/2004 | Phillips |
| 2004/0127476 A1 | 7/2004 | Kershman et al. |
| 2005/0031693 A1 | 2/2005 | Babcock et al. |
| 2005/0070516 A1 | 3/2005 | Wilson |
| 2005/0080075 A1 | 4/2005 | Nichols et al. |
| 2005/0096296 A1 | 5/2005 | Fikstad et al. |
| 2005/0096365 A1 | 5/2005 | Fikstad et al. |
| 2005/0100608 A1 | 5/2005 | Ebert |
| 2005/0101517 A1 | 5/2005 | De Nijs et al. |
| 2005/0171193 A1 | 8/2005 | Chen et al. |
| 2005/0176692 A1 | 8/2005 | Amory et al. |
| 2005/0209345 A1 | 9/2005 | Charman |
| 2005/0220825 A1 | 10/2005 | Funke et al. |
| 2005/0269251 A1 | 12/2005 | Cork |
| 2005/0287203 A1 | 12/2005 | Nijs De et al. |
| 2005/0287212 A1 | 12/2005 | Dong et al. |
| 2006/0003002 A1 | 1/2006 | Fikstad et al. |
| 2006/0034937 A1 | 2/2006 | Patel |
| 2006/0051406 A1 | 3/2006 | Parmar |
| 2006/0106004 A1 | 5/2006 | Brody et al. |
| 2006/0142257 A1 | 6/2006 | Nieschlag |
| 2007/0110777 A1 | 5/2007 | Joabsson et al. |
| 2007/0134336 A1 | 6/2007 | Worle et al. |
| 2007/0232548 A1 | 10/2007 | Taneja |
| 2008/0020053 A1 | 1/2008 | Persson et al. |
| 2008/0217692 A1 | 9/2008 | Anderson et al. |
| 2008/0317844 A1 | 12/2008 | Dudley et al. |
| 2008/0317850 A1 | 12/2008 | Hewitt et al. |
| 2009/0074859 A1* | 3/2009 | Patel .......................... 424/457 |
| 2010/0136105 A1 | 6/2010 | Chen et al. |
| 2010/0137271 A1 | 6/2010 | Chen et al. |
| 2010/0173882 A1 | 7/2010 | Giliyar et al. |
| 2011/0039814 A1 | 2/2011 | Huatan et al. |
| 2011/0142945 A1* | 6/2011 | Chen et al. ............... 424/489 |
| 2011/0251167 A1* | 10/2011 | Dudley et al. ............. 514/178 |
| 2012/0135074 A1* | 5/2012 | Giliyar et al. ............. 424/457 |
| 2012/0148675 A1 | 6/2012 | Chickmath et al. |
| 2012/0244215 A1 | 9/2012 | Giliyar et al. |
| 2012/0322780 A1* | 12/2012 | Giliyar et al. ............. 514/178 |
| 2013/0052263 A1 | 2/2013 | Fikstad et al. |
| 2013/0225544 A1 | 8/2013 | Nachaegari |

FOREIGN PATENT DOCUMENTS

| | | |
|---|---|---|
| EP | 0184942 | 6/1986 |
| EP | 0724877 | 6/2000 |
| EP | 1624855 | 12/2004 |
| EP | 1624855 | 8/2006 |
| EP | 1879456 | 1/2008 |
| EP | 2000130 | 12/2008 |
| GB | 2098865 | 12/1982 |
| JP | S 5770824 | 5/1982 |
| JP | 01139526 | 6/1989 |
| JP | 5194209 | 3/1993 |
| JP | 07041422 | 2/1995 |
| JP | 09241152 | 9/1997 |
| JP | 11049664 | 2/1999 |
| JP | 11152227 | 6/1999 |
| JP | 2001500368 | 1/2001 |
| JP | 2001508445 | 6/2001 |
| JP | 2001514626 | 9/2001 |
| JP | 2002510311 | 4/2002 |
| JP | 2002520377 | 7/2002 |
| WO | WO 82/01649 | 5/1982 |
| WO | WO 84/02076 | 6/1984 |
| WO | WO 88/00059 | 1/1988 |
| WO | WO 93/06921 | 4/1993 |
| WO | WO 93/25192 | 12/1993 |
| WO | WO 94/25068 | 11/1994 |
| WO | WO 95/34287 | 12/1995 |
| WO | WO 96/17597 | 6/1996 |
| WO | WO 97/04749 | 2/1997 |
| WO | WO 97/40823 | 11/1997 |
| WO | WO 97/48382 | 12/1997 |
| WO | WO 98/30205 | 7/1998 |
| WO | WO 98/33512 | 8/1998 |
| WO | WO 98/50077 | 11/1998 |
| WO | WO 99/00111 | 1/1999 |
| WO | WO 99/29300 | 6/1999 |
| WO | WO 99/40904 | 8/1999 |
| WO | WO 00/03753 | 1/2000 |
| WO | WO 00/16749 | 3/2000 |
| WO | WO 00/25772 | 5/2000 |
| WO | WO 00/37057 | 6/2000 |
| WO | WO 00/50007 | 8/2000 |
| WO | WO 00/57859 | 10/2000 |
| WO | WO 00/59482 | 10/2000 |
| WO | WO 0057918 | 10/2000 |
| WO | WO 00/72825 | 12/2000 |
| WO | WO 00/76482 | 12/2000 |

(56) References Cited

FOREIGN PATENT DOCUMENTS

| WO | WO 01/01960 | 1/2001 |
|---|---|---|
| WO | WO 01/12155 | 2/2001 |
| WO | WO 01/21154 | 3/2001 |
| WO | WO 01/28555 | 4/2001 |
| WO | WO 01/37808 | 5/2001 |
| WO | WO 01/49262 | 7/2001 |
| WO | WO 02/39983 | 5/2002 |
| WO | WO 03/068186 | 8/2003 |
| WO | WO 2004/087052 | 10/2004 |
| WO | WO 2004/105694 | 12/2004 |
| WO | WO 2005/041929 | 5/2005 |
| WO | WO 2006/119498 | 11/2006 |
| WO | WO 2007/018943 | 2/2007 |

OTHER PUBLICATIONS

Zhi et al., "Effects of dietary fat on drug absorption," Clinical Pharmacology & Therapeutics 58(5): pp. 487-491 (Nov. 1995).
Supplementary EP Search Report for EP04753162 dated Apr. 13, 2010.
PCT/US04/16286 International Search Report dated May 8, 2006.
PCT/US2011/064495; filed Dec. 12, 2011; Lipocine Inc.; International Search Report dated Sep. 27, 2012.
U.S. Appl. No. 13/029,989, filed Feb. 17, 2011; Feng-Jing Chen; office action dated Dec. 4, 2012.
Beatch, G.N. et al., "Ventricular Fibrillation, an Uncontrolled Arrhythmia Seeking New Targets," Drug Dev. Res 55:45-52 (2002).
Goncharova et al., "Preparation of Testosterone Esters," Pharmaceutical Chemistry Journal 7(7):427-428 (Jul. 1973).
Houwing,N.S et al., "Pharmacokinetic Study in Women of Three Different Doses of a New Formulation of Oral Testosterone Undecanoate, Andriol Testocaps," Pharmacotherapy 23(10):1257-1265 (2003).
Hutchison,K. "Digestable Emulsions and Microenulsions for Optimum Oral Delivery of Hydrophobic Drugs," Bulletin Technique Gattefosse 87: 67-74 (1994).
Langer, "New Methods of Drug Delivery," Science 249(4976); pp. 1527-1533 (Sep. 1990).
Merck Index (14$^{th}$ ed), "Fenofibrate" (Monograph 3978), Merck & Co, Inc., 2006, p. 679-680.
Merck Index (14$^{th}$ ed), "Vitamin E" (Monograph 10021), Merck & Co, Inc., 2006, p. 1726.
Nieschlag et al., "Plasma Androgen Levels in Men after Oral Administration of Testosterone or Testosterone Undecanoate," Acta Endocrinologica 79(2): pp. 366-374 (1975) (Abstract).
Remington: The Science and Practice of Pharmacy (19$^{th}$ Ed), 1995, "Surfactant Properties in Solution and Micelle Formation" pp. 272-276.
Saudek et al., "A preliminary trial of the programmable implantable medication system for insulin delivery," N.End.J.Med 321:574-579 (Aug. 31, 1989).
Schott, "Comments on Hydrophile-Lipophile Balance Systems," J.Pharm.Sci. 79(1):87-88 (1990).
Schnabel et al., "The effect of food composition on serum testosterone levels after oral administration of Andriol Testocaps," Clinical Endocrinology 66(4): pp. 579-585 (2007).
Shanghai Pi Chemicals Ltd. "Material Safety Data Sheet: Testosterone Undecanoate," Online 2007, retrieved Jun. 3, 2009 from http://www.pipharm.com/products/msds/msds-13457.pdf.
Alvarez, F. J. and Stella, V. J., "The Role of Calcium Ions and Bile Salts on the Pancreatic Lipase-Catalyzed Hydrolysis of Triglyceride Emulsions Stabilized with Lecithin", Pharmaceutical Research, 6(6), 449-457 (1989).
Aungst (2000), "Intestinal Permeation Enhancers," Journal of Pharmaceutical Sciences 89(4):429-442.
Baluom et al. (1998), "The Importance of Intestinal Residence Time of Absorption Enhancer on Drug Implication on Formulative Considerations," International Journal of Pharmaceutics 176:21-30.
Bates, T. R. and Sequeira, J. A., "Bioavailability of Micronized Griseofulvin from Corn Oil-in-Water Emulsion, Aqueous Suspension, and Commercial Tablet Dosage Forms in Humans", Journal of Pharmaceutical Sciences, 64(5), 793-797(1975).
Bernkop-Schnurch (1998), "The Use of Inhibitory Agents to Overcome the Enzymatic Barrier to Perorally Administered Therapeutic Peptides and Proteins," Journal of Controlled Release 52:1-16.
Charman, W. N., Porter, C.J.H., Mithani, S., and Bressman, J.B., "Physicochemical and Physiological Mechanisms for the Effects of Food on Drug Absorption: The Role of Lipids and pH", Journal of Pharmceutical Sciences, 86(3), 269-282 (1997).
Gennaro, A. R., Remington's Pharmaceutical Sciences, Chapter 20, 293-300 (1985).
Horter, D. and Dressman, J.B., "Influence of Physicochemical Properties on Dissolution of Drugs in the Gastrointestinal Tract", Advanced Drug Delivery Reviews 25, 3-14 (1997).
Humberstone, A. J. and Charman, W. N. "Lipid-based Vehicles for the Oral Delivery of Poorly Water Soluble Drugs", Advanced Drug Delivery Reviews, 103-128 (1997).
Johnson, L. R., "Gastrointestinal Physiology", Department of Physiology, University of Texas Medical School, Houston, Texas, 25-26, 93, 106, 133-134, 136-137 (1997).
Julien, R.M., A Primer of Drug Action (Ninth Edition), 2001, p. 5-6.
LeCluyse et al. (1997), "In Vitro Models for Selection of Development Candidates. Permeability Studies to Define Mechanisms of Absorption Enhancement," Advanced Drug Delivery Reviews 23:163-183.
Leichtnam et al., "Testosterone Hormone Replacement Therapy: State-of-the-Art and Emerging Technology," Pharma. Res. 23(6): 1117-1132 (2006).
MacGregor, K. J. et al., "Influence of Lipolysis on Drug Absorption From the Gastro-intestinal Tract", Advanced Drug Delivery Reviews 25, 33-46 (1997).
Muranishi (1977), "Potential Absorption of Heparin from the Small Intestine and the Large Intestine in the Presence of Monoolein Mixed Micelles," Chem. Pharm. Bull. 24(5):1159-1161.
Muranishi (1990), "Absorption Enhancers," Critical Reviews in Therapeutic Drug Carrier Systems 7(1):1-33.
Osol, ed., Remington's Pharmaceutical Sciences (15th ed), 1975, Mack Publishing Co., pp. 327-339, 1452-1456.
Pouton, C. W., "Formulation of Self-Emulsifying Drug Delivery Systems", Advanced Drug Delivery Reviews 25, 47-58 (1997).
Reymond, J. and Sucker, H., "In Vitro Model for Ciclosporin Intestinal Absorption in Lipid Vehicles", Pharmaceutical Research, 5(10), 677-679.
Tarr, D. T. and Yalkowsky, S. H. "Enhanced Intestinal Absorption of Cyclosporine in Rats Through the Reduction of Emulsion Droplet Size", Pharmaceutical Research, 6(1), 40-43 (1989).
Treat, et al., "Liposomes in the Therapy of Infectious Diseases and Cancer", Lopez-Berestein and Fidler (eds.), Liss, New York, (1989), 353-365.
Winne, D., "Dependence of Intestinal Absorption in Vivo on the Unstirred Layer", Archives of Pharmacology, 304, 175-181 (1978).
PCT/US2011/062538; filed Nov. 30, 2011; Chandrashekar Giliyar, et al.; International Search Report mailed Jun. 26, 2012.
U.S. Appl. No. 12/957,206, filed Nov. 30, 2010; Chandrashekar Giliyar; office action dated Mar. 1, 2013.
U.S. Appl. No. 13/029,989, filed Feb. 17, 2011; Feng-Jing Chen; office action dated Mar. 19, 2013.
U.S. Appl. No. 13/029,989, filed Feb. 17, 2011; Feng-Jing Chen; office action dated Nov. 18, 2013.
Frey et al.; Bioavailability of Oral Testosterone in Males; European Journal of Clinical Parmacology; Jun. 30, 1979; pp. 345-349; vol. 16; Springer-Verlag.
U.S. Appl. No. 12/957,206, filed Nov. 30, 2016; Giliyar Chandrashakar.
U.S. Appl. No. 12/350,930, filed Jan. 8, 2009; Giliiyar Chandrashakar.
U.S. Appl. No. 13/843,403, filed Mar. 15, 2013; Sadish Kumar Nachaegari.
U.S. Appl. No. 12/965,703, filed Dec. 10, 2010; Basawaraj Chickmath; office action dated Feb. 27, 2014.

(56) References Cited

OTHER PUBLICATIONS

S1 SEC filing (Securities and Exchange Commission) for Clarus Therapeutics, Inc.; filed May 23, 2014 with the Securities and Exchange Commission; 207 pages.

Androgel® Product Label and Medication Guide; May 2013; Labeler—AbbVie Inc.; Revised Oct. 2013; 28 pages.

Depo-Testosterone® Product Label and Medication Guide; Sep. 2006; Labeler—Pharmacia & Upjohn Company; Revised Aug. 2013; 12 pages.

Androderm® Product Label and Medication Guide; 1995; Labeler—Watson Pharma, Inc.; Revised Nov. 2013; 23 pages.

Testim® Product Label and Medication Guide; Sep. 2009; Labeler—A-S Medications Solutions LLC; Revised Jun. 2013; 17 pages.

U.S. Appl. No. 12/965,703, filed Dec. 10, 2010; Basawaraj Chickmath; office action dated Jul. 1, 2014.

PCT Application PCT/US14/30604; filing date Apr. 17, 2014; Lipocine Inc.; International Search Report mailed Aug. 5, 2014.

Torpac Inc.; Capsule Size Chart, Metric Table and English Table; www.torpac.com ; 2000 (retrieved from website Sep. 2014); 3 pages; Torpac Inc., Fairfield, New Jersey.

U.S. Appl. No. 12/957,206, filed Nov. 30, 2010; Chandrashekar Giliyar; office action dated Sep. 15, 2014.

U.S. Appl. No. 12/957,206, filed Nov. 30, 2010; Chandrashekar Giliyar; office action dated Jul. 18, 2013.

U.S. Appl. No. 12/326,711, filed Dec. 2, 2008; Mahesh Patel; office action dated Jul. 19, 2013.

\* cited by examiner

HIGH-STRENGTH TESTOSTERONE UNDECANOATE COMPOSITIONS

PRIORITY DATA

This application is a continuation-in-part of U.S. patent application Ser. No. 12/957,206, filed on Nov. 30, 2010 and of Patent Cooperation Treaty Application Serial No. PCT/US2011/62538, filed on Nov. 30, 2011, each of which are incorporated herein by reference.

FIELD OF THE INVENTION

The present invention relates to testosterone undecanoate containing pharmaceutical compositions and oral dosage capsules as well as associated methods. Accordingly, this invention involves the fields of chemistry, pharmaceutical sciences, medicine and other health sciences.

BACKGROUND OF THE INVENTION

Male hypogonadism is a serious condition affecting mostly aging men. The common reasons for hypogonadism in men could be physiological abnormality involving among other factors, improper functioning or growth of the gonads and/or the pituitary-hypothalamus regulatory systems, and aging. Many of the abnormalities that are identified to be commonly associated with the low or decreased testosterone levels include impaired sexual function and/or libido, metabolic syndrome which may be a combination of abdominal obesity, high blood pressure, insulin resistance, lipid disorders; high risk of cardiovascular diseases; reduced bone mass/mineral density and muscle weakness and or degeneration affecting the musculoskeletal system. Other effects of low testosterone levels include negative changes in body composition, depression and other psychological disorders. The average human male produces 4-7 mg of testosterone per day in a circadian pattern, with maximal plasma levels attained in early morning and minimal levels in the evening. It is generally recognized that in a normal adult man of age 17 to 54 years, the serum total testosterone (T) is between about 300 ng/dL to about 1100 ng/dL and this range is referred to as the eugonadal range. Restoration of testosterone levels to the eugonadal range typically corrects many of the cited clinical abnormalities associated with hypogonadism or low testosterone levels.

While oral administration is the most preferred and patient friendly route for administration, the effective oral delivery of testosterone as testosterone and its esters remains a challenge. This is due to extremely poor bioavailability of testosterone, which requires very high dosing as well as frequent dosing due to the short serum half-life. These problems with orally administered testosterone products are primarily due to first pass metabolism. Further, direct oral delivery of testosterone has also been known to cause enzyme induction resulting in potential drug-drug interactions.

Currently, modified testosterones, in form of a methyl analogue of testosterone, and as an undecanoate ester, testosterone undecanoate (TU) are available for oral administration for patients in need of testosterone therapy. However, liver damage including cholestasis, peliosis hepatitis, nodular regenerative hyperplasia, and primary hepatic tumors has been reported with use of methyl testosterone. Testosterone undecanoate is a prodrug which gets converted to testosterone in vivo. Testosterone undecanoate containing products are available in some countries as liquid filled soft-gelatin capsule containing 40 mg of fully solubilized testosterone undecanoate. Testosterone undecanoate is extremely lipophilic (calculated logP of ~6.5) with a water solubility of <0.3 ng/ml and a melting point around 62° C. It is generally believed that in order to promote lymphatic absorption for better safety profile and to facilitate effective oral delivery of testosterone undecanoate, the testosterone undecanoate must be presented in a bioacceptable solubilizer. Accordingly, research continues into the development of testosterone oral delivery products that can have high drug load and provide for practical unit oral dosage forms.

SUMMARY OF THE INVENTION

The present disclosure is drawn to pharmaceutical compositions and oral dosage capsules containing testosterone undecanoate, as well as related methods. In one embodiment, a pharmaceutical capsule for oral delivery is provided. The capsule includes a capsule shell and a capsule fill. The capsule fill can include a solubilizer and about 14 wt % to about 35 wt % testosterone undecanoate based on the total weight of the capsule fill. In some aspects, the oral dosage capsule is such that upon a single oral administration to a male subject of one or more capsules with a total testosterone undecanoate daily dose of about 350 mg to about 650 mg it provides a ratio of serum testosterone $C_{max}$ to serum testosterone $C_{ave}$ of about 2.7 or less.

In another embodiment, a method for providing a serum concentration of testosterone within a target serum testosterone concentration $C_{ave}$ range for a male subject is provided. The method can include the step of orally administering to the male subject a daily dose of a testosterone undecanoate-containing composition. The testosterone undecanoate can comprise about 14 wt % to about 35 wt % of the testosterone undecanoate-containing composition and the daily dose provided can be about 350 mg to about 420 mg of testosterone undecanoate to the male subject.

In yet a further embodiment, a method for providing a serum concentration of testosterone within a target serum testosterone concentration $C_{ave}$ range for a male subject is provided. The method can include the step of orally administering to the male subject an initial regimen including a daily dose of a testosterone undecanoate-containing composition. The testosterone undecanoate can comprise about 14 wt % to about 35 wt % of the testosterone undecanoate-containing composition and the daily dose provided can be about 350 mg to about 650 mg of testosterone undecanoate to the male subject. After the initial regimen, the method can include a step of determining the serum testosterone concentration for the male subject on at least one titration node day within the initial regimen. The method further can include the step of orally administering to the male subject a maintenance regimen including a daily dose of testosterone undecanoate-containing composition that comprises about 14 wt % to about 35 wt % of the testosterone undecanoate. The maintenance regimen can provide a daily dose of testosterone undecanoate to the subject based on the serum testosterone concentration determined by a titration metric on the at least one titration node day of the initial regimen and the said maintenance daily dose can be sufficient to provide a serum testosterone plasma concentration within the target range. The method can provide a steady state ratio of serum testosterone $C_{max}$ to $C_{ave}$ of 2.7 or less.

The applicants of the present invention have found that capsule fill compositions with a lower TU loading of less than 14% w/w are unsuitable for optimal activity due to inadequate bioavailability which also leads to larger dosage forms/doses for therapy in treatment of symptoms related to male hypogonadism. Consistent with the compositions of the present invention, higher loading dosage forms, i.e. those with ≥14% w/w of TU based on total capsule fill, resulted in a superior $C_{ave}$ per mg testosterone undecanoate administered, thus providing improved performance of oral testosterone undecanoate as a testosterone therapy.

Further, it was also found that it is not necessary to fully dissolve the testosterone undecanoate in the capsule fill, but rather only about at least 80 wt % of the testosterone undecanoate may need to be dissolved with at least 5% of testosterone undecanoate possibly needing to remain undissolved in order to achieve a desired and efficient $C_{ave}$ per mg of testosterone undecanoate administered. Therefore, in one embodiment in order to facilitate improved activity, an oral capsule with TU loading in the range of about 14 wt % to about 18% is provided in which no more than 80 wt % of the TU in the capsule fill is dissolved. This capsule can result in dose normalized $C_{max}$ suggesting superior bioavailability yet manageable $C_{max}$ for effective therapeutics.

DETAILED DESCRIPTION

Before the present testosterone undecanoate compositions, oral dosage capsules and related methods of use are disclosed and described, it is to be understood that this invention is not limited to the particular process steps and materials disclosed herein, but is extended to equivalents thereof, as would be recognized by those ordinarily skilled in the relevant arts. It should also be understood that terminology employed herein is used for the purpose of describing particular embodiments only and is not intended to be limiting.

It should be noted that, the singular forms "a," "an," and, "the" include plural referents unless the context clearly dictates otherwise. Thus, for example, reference to "an excipient" includes reference to one or more of such excipients, and reference to "the carrier" includes reference to one or more of such carriers.

Definitions

As used herein, the term "treatment," when used in conjunction with the administration of pharmaceutical compositions and oral dosage capsules containing testosterone undecanoate, refers to the administration of the oral dosage capsules and pharmaceutically acceptable composition to subjects who are either asymptomatic or symptomatic. In other words, "treatment" can both be to reduce or eliminate symptoms associated with a condition present in a subject, or it can be prophylactic treatment, i.e. to prevent the occurrence of the symptoms in a subject. Such prophylactic treatment can also be referred to as prevention of the condition.

As used herein, the terms "formulation" and "composition" are used interchangeably and refer to a mixture of two or more compounds, elements, or molecules. In some aspects the terms "formulation" and "composition" may be used to refer to a mixture of one or more active agents with a carrier or other excipients. Furthermore, the term "dosage form" can include one or more formulation(s) or composition(s) provided in a format for administration to a subject. When any of the above terms is modified by the term "oral" such terms refer to compositions, formulations, or dosage forms formulated and intended for oral administration to subjects.

As used herein, the term "fatty acid" refers to unionized carboxylic acids with a long aliphatic tail (chain), either saturated or unsaturated, conjugated or non-conjugated.

Unless otherwise specified, the term $C_8$ to $C_{22}$ fatty acid glycerides refers to a mixture of mono-, di-, and/or tri-glycerol esters of medium to long chain ($C_8$ to $C_{22}$) fatty acids.

As used herein, the term "dispersant" refers to any pharmaceutically acceptable additive that enables the contents of the compositions and/or oral dosage capsules to disperse in an aqueous medium. The extent of dispersion in an aqueous medium can be determined spectrophotometrically from the absorbance exhibited by the dispersion at a wavelength of about 400 nm. For example, the dispersion of the composition (with or without the testosterone undecanoate) of the current invention in about 0.2 mM sodium lauryl sulphate solution in water, has an absorbance of about 0.6 or less at about 400 nm wavelength, when the ratio of the composition to the sodium lauryl sulphate solution is about 1:2000. In a specific embodiment, the dispersion of the composition (with or without the testosterone undecanoate) of the current invention in about 0.2 mM sodium lauryl sulphate solution in water, has an absorbance of about 0.3 or less at about 400 nm wavelength, when the ratio of the composition to the sodium lauryl sulphate solution is about 1:5000. In another embodiment, the composition can produce a fine dispersion upon dilution in an aqueous medium without the need of a hydrophilic surfactant.

Further, as used herein, the dispersant of the current invention is at least one selected from the group of hydrophilic surfactant or lipophilic surfactant. In one embodiment, the dispersant includes a hydrophilic surfactant.

As used herein, the term "solidifying agent" or "solidifying additive" are used interchangeably and refer to a pharmaceutically acceptable additive that is in a solid physical state at 20° C. Similarly, a "solid lipophilic additive" refers to a lipophilic compound or component that is in a solid physical state at 20° C. and/or renders the composition or dosage form non-liquid, such as solid or semi-solid.

As used herein, the terms "solubilized" and "solubility," when used to describe the state of testosterone undecanoate with respect to a composition and/or capsule fill, refer to the absence of testosterone undecanoate crystals in the composition or oral dosage form when observed under hot-stage microscope over a temperature of about 25° C. to about 65° C., or the absence of crystalline testosterone undecanoate melting related peak (about 62 to about 65° C.). when the composition or oral dosage form is subjected to differential scanning calorimetry. Similarly, the solubility of testosterone undecanoate in a particular compound, e.g. a solubilizer, is the amount of testosterone undecanoate dissolved to form a visibly clear solution at a specified temperature such as about 25° C. or about 37° C. With this definition in mind, compositions having crystalline forms of testosterone undecanoate at about room temperature would be considered to have an unsolubilized fraction and a solubilized fraction of testosterone undecanoate which fraction includes testosterone undecanoate in a solid state that is not crystalline such as amorphous and solid solution which are solubilized but undissolved.

As used herein, "undissolved" or "non-dissolved" can be used interchangeably and when one is used to describe the state of testosterone undecanoate with respect to a composition and/or capsule fill refers to the testosterone undecanoate in a non-liquid testosterone undecanoate-containing composition that is solubilized (such as non-crystalline) and non-solubilized such as crystalline TU. The solubility of TU in the composition can be estimated based on the individual solubility in the composition components. For solubilizers that are viscous or non-liquid at room temperature, TU solubility in the composition at room temperature (RT) may be estimated based on the observed values at higher temperature such as at 37° C.

As used herein, "dissolved" when used to describe the state of testosterone undecanoate (TU) with respect to a composition or capsule fill refers to a testosterone undecanoate-containing liquid solution having no undissolved testosterone undecanoate.

As used herein, the term "lipophilic," refers to compounds that are not freely soluble in water; and the term "lipophilic surfactant" refers to surfactants that have HLB values of about 10 or less. Conversely, the term "hydrophilic" refers to compounds that are soluble in water; and term "hydrophilic surfactant" refers to surfactants that have HLB values of more than about 10.

As used herein, the term "ionizable fatty acid" refers to a fatty acid compound that changes its HLB as a function of pH. For example oleic acid is predominantly lipophilic at lower pH values (such as those found in the stomach) but becomes a predominantly hydrophilic at higher pH values (such as those found in the intestine).

As used herein, "subject" refers to a mammal that may benefit from the administration of a drug composition or method of this invention. Examples of subjects include humans. In one aspect, the subject can be a human male. In another embodiment, the subject can be a hypogonadal male. As used herein, the testosterone deficiency or hypogonadism in a male human subject (hypogonadal male) refers to a condition wherein the average baseline plasma testosterone concentration (T-$C_{avg\text{-}B}$) is about 300 ng/dL or less. However in some instances, testosterone deficiency or hypogonadism in a male human subject refers to a condition wherein the average baseline plasma testosterone concentration is about 400 ng/dL or less.

A used herein, a "responder" is a subject who responds to exogenous oral testosterone undecanoate therapy. "Responder analysis" is the assessment of the effectiveness of testosterone undecanoate therapy in a group of subjects deemed to get benefits of oral TU therapy.

As used herein, "group" or "group of subjects" refers to a collection of at least 24 human male subjects who receive and respond to exogenous oral administration of the compositions disclosed herein, namely testosterone undecanoate-containing compositions. In one aspect, the group can include at least 100 or at least 300 male subjects. In another aspect, the group can include at least 1000 male subjects. In another embodiment, the subjects can be hypogonadal subjects.

The term "oral administration" represents any method of administration in which an active agent can be administered by swallowing, chewing, or sucking of the dosage form. The composition of the current inventions can be admixed with food or drink prior to being orally consumed.

As used herein, a "dosing regimen" or "regimen" such as an "initial dosing regimen" or a "maintenance dosing regimen" refers to how, when, how much, and for how long a dose of the compositions of the present invention can be administered to a subject. For example, an initial dosing regimen for a hypogonadal male subject may provide for a total daily dose of 600 mg administered in two divided doses at least 12 hours apart (e.g. once with breakfast and once with dinner) with meals having about 25-55 g of fat content repeated daily for 30 days.

As used herein, "daily dose" refers to the amount of active agent (e.g. testosterone undecanoate) administered to a subject over a 24 hour period of time. The daily dose can be administered two or more administrations during the 24 hour period. In one embodiment, the daily dose provides for two administrations in a 24 hour period. With this in mind, an "initial dose" or initial daily dose" refers to a dose administered during the initial regimen or period of a dosing regimen. An initial dose includes both the very first dose during the initial regimen as well as the subsequent doses during the same initial regimen. Similarly, a "maintenance dose" or "maintenance daily dose" refers to a dose administered during a maintenance regimen of a dosing regimen. It is worth noting that the maintenance dose follows a dose titration based on the serum testosterone determination on a titration node day, however the maintenance dose does not need to be of a different quantity as the initial dose or the previous maintenance dose (in the case of multiple titrations).

As used herein, "non-liquid" when used to refer to the state of a composition disclosed herein refers to the physical state of the composition as being a semi-solid or solid.

As used herein, "solid" and "semi-solid" refers to the physical state of a composition that supports its own weight at standard temperature and pressure, and has adequate viscosity or structure to not freely flow. Semi-solid materials may conform to the shape of a container under applied pressure.

As used herein, "titration" or "dose titration" or "dose adjustment" are used interchangeably and refer to an increase or decrease of the total daily dose of testosterone undecanoate administered to a subject, typically based on the response of the subject to the exogenous administered testosterone undecanoate. The dose can be increased or decreased based on the measurement of serum testosterone concentration after a steady state has been achieved.

As used herein, "steady state" refers to the achievement of a stable response in serum total testosterone levels to exogenously administered testosterone undecanoate, typically achieved after at least 15 days following the start of a dosing regimen.

In some embodiments, the titration can also include the adjustment of the way the total daily dose is administered such as whether it is administered as two or three doses within a 24 hour period, whether it is administered with a meal, with a meal with a particular fat content, or at a particular hour of the day.

As used herein, "initial daily dose" (IDD) or "Daily dose of the initial regimen" is a dose of testosterone undecanoate administered daily to a subject in need of testosterone therapy. The initial daily dose may be administered in two or more intervals over a 24 hour period, e.g. twice-a-day. Similarly, "maintenance daily dose" or "daily dose of the maintenance regiment" is a dose of testosterone undecanoate administered daily to a subject in need of testosterone therapy as determined based on measurement of the titration node day titration metric and is the daily dose going forward within a few days of measurement unless a dose change is needed based on a another titration node day measurements. During a maintenance regime there may be two or more daily doses administered which at some point during the regime would be considered to be the maintenance daily dose.

As used herein, "titration node" or "titration node day" are used interchangeably and refer to a day on which a serum sample is drawn from a subject for measurement of the serum testosterone concentrations in order to determine whether a testosterone undecanoate dose titration is necessary and what the titration type might need to be. The measured serum testosterone levels may also be used to determine dose a titration metric to be utilized in deciding dose titration needs for an individual subject. As dosing regimens can include one or more titration node day the term may refer to a first titration node during a dosing regimen (e.g. between the initial dosing regimen and the maintenance dosing regimen) or it can refer to a subsequent titration node day between a maintenance dosing regimen and a subsequent maintenance dosing regimen.

As used herein, "titration day" refers to the day when administration of a newly titrated (adjusted) dose is initiated.

It should be noted that one or more titrations can be conducted to arrive at a maintenance daily dose in a maintenance regimen. Thus, the maintenance daily dose and regimen is considered to be the dose based on the last or most recent titration.

As used herein, "titration metric" is a pharmacokinetic (PK) parameter determined from a serum sample on a titration node day. The PK parameter used as the titration metric can include the serum testosterone $C_{max}$, $C_{avg}$, $C_{min}$, $C_{pre\text{-}dose}$ or $C_t$ (serum concentration at a particular time of day). The titration metric can be used to aid in the determination of whether a dose titration is necessary, its magnitude, and other factors possibly included in the titration adjustment.

As used herein, the terms "release" and "release rate" are used interchangeably to refer to the discharge or liberation of a substance, including without limitation a drug, from the dosage form into a surrounding environment such as an aqueous medium either in vitro or in vivo.

As used herein, an "effective amount" or a "therapeutically effective amount" of a drug refers to a non-toxic, but sufficient amount of the drug, to achieve therapeutic results in treating a condition for which the drug is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a somewhat subjective decision. The determination of an effective amount is well within the ordinary skill in the art of pharmaceutical sciences and medicine. See, for example, Meiner and Tonascia, "Clinical Trials: Design, Conduct, and Analysis," *Monographs in Epidemiology and Biostatistics*, Vol. 8 (1986), incorporated herein by reference.

As used herein, the term "delayed release" refers to the release into an aqueous solution of the testosterone undecanoate from the composition or oral dosage form in a time delayed manner attributed either to the inherent nature of the composition or to a coating which may surround the composition or the oral dosage form. A traditional gelatin or non-gelatin non-enteric capsule shell does not alone constitute a delayed release mechanism. In one embodiment, the delayed release is such that about 20% or less of the testosterone undecanoate is released within the first 15 minutes after the composition is contacted by the aqueous solution.

The terms "plasma testosterone concentration," "testosterone concentration in the blood," and "serum testosterone concentration" are used interchangeably and refer to the "total" testosterone concentration which is the sum of the bioavailable testosterone including free and protein-bound testosterone concentrations. As with any bio-analytical measure, for increased consistency the method employed to measure initial serum testosterone levels should be consistent with the method used to monitor and re-measure serum testosterone levels during clinical testing and testosterone therapy for a subject. Unless otherwise stated, "testosterone concentration" refers to serum total testosterone concentration.

As used herein, of the average serum testosterone concentration can be determined using methods and practices known in the art. For example, the average baseline plasma testosterone concentration of a human male is the arithmetic mean of the total plasma testosterone concentrations determined on at least two consecutive time points that are reasonably spaced from each other, for example from about 1 hour to about 168 hours apart. In a particular case, the plasma testosterone concentration can be determined on at least two consecutive times that are about 12 hours to about 48 hours apart. In another particular method, the plasma testosterone concentration of the human male can be determined at a time between about 5 o'clock and about 11 o'clock in the morning. Further, the plasma testosterone concentration can be the determined by standard analytical procedures and methods available in the art, such as for example, automated or manual immunoassay methods, liquid chromatography or liquid chromatography-tandem mass spectrometry (LC-MSMS) etc.

As used herein, the term $AUC_{0\text{-}t}$ is the area under the curve of a plasma-versus-time graph determined for the analyte from the time 0 to time "t".

As used herein, the term "$C_{avg}$," "$C_{ave}$," or "C-average" are used interchangeably, and is determined as the $AUC_{0\text{-}t}$ or the mean AUC divided by the time period (t). For example, $C_{avg\text{-}8h}$ is the average plasma concentration over a period of 8 hours post-dosing determined by dividing the $AUC_{0\text{-}8}$ value by 8. Similarly, $C_{avg\text{-}12h}$ is the average plasma concentration over a period of 12 hours post-dosing determined by dividing the $AUC_{0\text{-}12}$ value by 12; $C_{avg\text{-}24h}$ is the average plasma concentration over a period of 24 hours post-dosing determined by dividing the $AUC_{0\text{-}24h}$ value by 24, and so on. Unless otherwise stated, all $C_{ave}$ values are considered to be $C_{ave\text{-}24h}$.

As used herein, "$C_t$," refers to the serum concentration of testosterone at time "t" prior to or after administration of the dosage of the current invention. The time "t" is generally in hours, unless otherwise specified. For example, a $C_t$ of "$C_{(-2 \, to \, 0)}$" refers to serum testosterone concentration measured in sample collected between the time of about 2 hours before and just immediately prior to dosage administration to the subject tested. Similarly, $C_t$ of "$C_{(2 \, to \, 4)}$" refers to serum testosterone concentration measured in sample collected between the time of about 2 hours and 4 hours after administration of a dosage to the subject tested.

As used herein "SIF" or "simulated intestinal fluid" refers to "intestinal fluid, simulated TS" in accordance with the USP. In one embodiment, the SIF does not contain pancreatic enzyme. In another embodiment, SIF may be a fed or fasted simulated intestinal aqueous solution comprising phosphatidyl choline and from about 2 mM to 20 mM bile salts.

As used herein "SGF" or "simulated gastric fluid" refers to "Gastric fluid, Simulated TS" in accordance with the USP. In one embodiment, the SGF does not contain the enzyme pepsin. In another embodiment, the SGF may also be a simple 0.1 N HCl solution in water.

As used herein, "free of" or "substantially free of" of a particular compound or compositions refers to the absence of any separately added portion of the referenced compound or composition. Free of or substantially free of can include the presence of 1 wt % or less (based on total composition weight) of the referenced compound which may be present as a component or impurity of one or more of the ingredients.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, levels and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges or decimal units encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Invention

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, variants, modifications, and equivalents as may be included within the spirit and scope of the invention as defined by the appended claims.

In one embodiment, a pharmaceutical capsule for oral delivery is provided. The capsule includes a capsule shell and a capsule fill. The capsule fill can include a solubilizer and about 14 wt % to about 35 wt % testosterone undecanoate based on the total weight of capsule fill. The oral dosage capsule is such that when a single oral administration to a male subject of one or more capsules with a total testosterone undecanoate daily dose of about 350 mg to about 650 mg it provides a ratio of serum testosterone $C_{max}$ to serum testosterone $C_{ave}$ of about 2.7 or less.

The compositions and oral dosage capsules of the present invention can be used to treat subjects, particularly human males, or even more particularly males who suffer from testosterone deficiency or hypogonadism. Accordingly, in one embodiment of the present invention, a method for providing a serum concentration of testosterone within a target serum testosterone concentration $C_{ave}$ range for a male subject is provided. The method includes the step of orally administering to the male subject a daily dose of a testosterone undecanoate-containing composition. The testosterone undecanoate comprises about 14 wt % to about 35 wt % of the testosterone undecanoate-containing composition and the daily dose provides about 350 mg to about 420 mg of testosterone undecanoate to the male subject. In one specific embodiment, the testosterone undecanoate comprises about 14 wt % to about 18 wt % of the testosterone undecanoate-containing composition.

Testosterone deficiency is typically associated with a particular condition that is the source or causes the deficiency. The compositions and oral dosage capsules of the present invention can be used to treat any condition associated with testosterone deficiency, including complete absence, of endogenous testosterone. Examples of conditions associated with testosterone deficiency that can be treated using the oral dosage capsules and/or compositions of the present invention include, but are not limited to congenital or acquired primary hypogonadism, hypogonadotropic hypogonadism, cryptorchidism, bilateral torsion, orchitis, vanishing testis syndrome, orchidectomy, Klinefelter's syndrome, post castration, eunuchoidism, hypopituitarism, endocrine impotence, infertility due to spermatogenic disorders, impotence, male sexual dysfunction (MSD) including conditions such as premature ejaculation, erectile dysfunction, decreased libido, and the like, micropenis and constitutional delay, penile enlargement, appetite stimulation, testosterone deficiency associated with chemotherapy, testosterone deficiency associated with toxic damage from alcohol, testosterone deficiency associated with toxic damage from heavy metal, osteoporosis associated with androgen deficiency, and combinations thereof.

Other conditions that can be treated by the compositions and oral dosage forms disclosed herein include idiopathic gonadotropin, LHRH deficiency, or pituitary hypothalamic injury from tumors, trauma, or radiation. Typically, these subjects have low serum testosterone levels but have gonadotropins in the normal or low range. In one embodiment, the compositions or oral dosage forms may be used to stimulate puberty in carefully selected males with clearly delayed puberty not secondary to pathological disorder. In another embodiment, the compositions and oral dosage forms may be used in female-to-male transsexuals in order to maintain or restore male physical and sexual characteristics including body muscle mass, muscle tone, bone density, body mass index (BMI), enhanced energy, motivation and endurance, restoring psychosexual activity etc. In some embodiments, the testosterone undecanoate compositions and oral dosage capsules may be useful in providing hormonal male contraception.

Additionally, testosterone therapy can also be used to improve the quality of life of subjects suffering from conditions such as decreased libido, diminishing memory, anemia due to marrow failure, renal failure, chronic respiratory or cardiac failure, steroid-dependent autoimmune disease, muscle wasting associated with various diseases such as AIDS, preventing attacks of hereditary angioedema or urticaria; andropause, and palliating terminal breast cancer. In some situations, certain biomarkers such as for example, increased SHBG levels, can be used to diagnose a subject who may be in need of testosterone therapy. These biomarkers can be associated with conditions/disease states such as anorexia nervosa, hyperthyroidism, hypogonadism, androgen insensitivity/deficiency, alcoholic hepatic cirrhosis, primary biliary cirrhosis, and the like.

Subjects that can be treated by the testosterone undecanoate compositions and oral dosage capsule of the present disclosure can be any human male in need thereof. In particular, in one embodiment, the human male may be at least 14 years of age. In another embodiment, the human male is an adult of at least age 30. In a further embodiment, the subject can be an adult male of at least age 50. In yet a further embodiment, the subject can be an adult male of at least age 60.

As discussed above, the compositions and oral dosage capsules disclosed herein can be used to treat testosterone deficiency in human males. In one embodiment, the human male being treated can have an average baseline plasma testosterone concentration of about 400 ng/dL or less. In another embodiment, the human male being treated can have an average baseline plasma testosterone concentration of about 350 ng/dL or less. In another embodiment, the human male being treated can have an average baseline plasma testosterone concentration of about 300 ng/dL or less. In another embodiment, the human male being treated can have an average baseline plasma testosterone concentration of about 250 ng/dL or less. In still another embodiment, the human male being treated can have an average baseline plasma testosterone concentration of about of about 190 ng/dL or less. In still a further embodiment, the human male has an average baseline plasma testosterone concentration of about 400 ng/dL or less, along with a co-morbid condition of insulin resistance.

Further, there are several biomarkers that can be used to identify patients who need testosterone therapy through the administration of the compositions and/or dosage forms of the current invention. Accordingly, in one embodiment, the human male being treated can have a low density lipoproteins (LDL) level in greater than about 130 mg/dL of blood. In another embodiment, the human male being treated can have a high density lipoproteins (HDL) level less than about 40 mg/dL of blood. In still another embodiment, the human male being treated can have a total cholesterol level greater than about 220 mg/dL of blood. In yet a further embodiment, the human male being treated can have an average TG (triglycerides) levels greater than 250 mg/dL of blood. In one embodiment, the testosterone undecanoate dosage forms of the current invention can be administered to human male whose bioavailable or free or un-bound plasma estradiol levels are about 20 pg/mL or less. In another embodiment, dosage forms of the current invention can be administered to human male who has a ratio of the bioavailable or free or unbound plasma testosterone level to the bioavailable or free or un-bound plasma estradiol level at about 100 or less.

The testosterone undecanoate compositions and oral dosage capsules of the current invention can be administered orally to a human male who has an average body mass index (BMI) of about 28 kg/m$^2$ or more. In another embodiment, the human male has an average BMI of about 30 kg/m$^2$ or more. In another embodiment, the human male has an average BMI of about 37 kg/m$^2$ or more. In a further embodiment, the subject male being treated can have a serum sex hormone binding globulin (SHBG) levels of about 40 nmol/L or more. In yet another embodiment, the human male being treated can have a serum SHBG levels of about 60 nmol/L or more.

It was found that the pharmaceutical compositions and oral dosage capsules of the present invention have the ability to provide for increased stability of the testosterone undecanoate present in the formulation. In particular, the pharmaceutical compositions and oral dosage capsules of the present invention can provide for superior stability with respect to the degradation of the testosterone undecanoate that can occur during storage as compared to other formulation containing lower testosterone undecanoate concentration. In one embodiment, the pharmaceutical compositions and oral dosage capsules of the present invention can have increased stability such that, when stored for a period of at least three months there is at least 20% less degradation of the testosterone undecanoate as compared to testosterone undecanoate containing compositions having less than 14 wt % testosterone undecanoate. In another embodiment, the pharmaceutical compositions and oral dosage capsules of the present invention can have increased stability such that, when stored for a period of at least three months there is at least 20% less degradation of the testosterone undecanoate as compared to testosterone undecanoate containing compositions having less than 16 wt % testosterone undecanoate.

Further, it has been discovered that the pharmaceutical compositions and oral dosage capsules disclosed herein can provide therapeutically effective treatment without the need to include oils, triglycerides, and/or hydrophilic surfactants. Accordingly, in one embodiment, the pharmaceutical compositions and oral dosage capsules can be free of oil. In another embodiment, the pharmaceutical composition and oral dosage capsules can be free of triglycerides. In one embodiment, the composition or capsule fill can comprise 25 wt % or less of total triglycerides. In one embodiment, the composition or capsule fill can be free of ionizable fatty acids. In another embodiment, the composition or capsule fill can be free of oleic acid. Without wishing to be bound by theory, it is believed that testosterone undecanoate-containing compositions or capsule fill that comprise greater than 25 wt % triglycerides have a higher dependence on digestion upon oral administration than do those in which the triglycerides comprise 25 wt % or less of the total composition or capsule fill. In one embodiment, the capsule fill can comprise 15 wt % or less of triglycerides. In yet another embodiment, the capsule fill can comprise 10 wt % or less of triglycerides. In yet a further embodiment, the capsule fill can comprise 5 wt % or less of triglycerides.

In yet a further embodiment, the pharmaceutical compositions and oral dosage capsules can be free of hydrophilic surfactants. In yet a further embodiment, the composition can include a hydrophilic surfactant as a dispersant and the hydrophilic surfactant can be present in an amount such that it does not appreciably solubilize the testosterone undecanoate in the composition. A hydrophilic surfactant is said to "not appreciably solubilize" testosterone undecanoate when it solubilizes 5 wt % or less of the testosterone undecanoate in the composition or the dosage form. In one embodiment, a hydrophilic surfactant is deemed to "not appreciably solubilize" testosterone undecanoate when it solubilizes 2 wt % or less of the testosterone undecanoate in the composition or oral dosage capsule. In all of these embodiments, the pharmaceutical compositions and oral dosage capsules can still be capable of providing the necessary dispersion and pharmacokinetics parameters to effectively treat testosterone deficiency.

The testosterone undecanoate can be present in the pharmaceutical compositions and oral dosage capsules in amounts sufficient to comprise 14 wt % to about 35 wt % of the composition or capsule fill. In one embodiment, the testosterone undecanoate can make up about 15 wt % to about 30 wt % of the composition or oral dosage capsule. In yet a further embodiment, the oral dosage capsule can comprise about 18 wt % to about 25 wt % of the composition or oral dosage capsule. In still a further embodiment, the compositions and/or capsule fill material can be such that the testosterone undecanoate comprises about 14 wt % to about 18 wt % of the total composition or capsule fill. In one embodiment, at least 35 wt % of the testosterone undecanoate in the composition or capsule fill can be in dissolved form. In yet another embodiment, at least about 66 wt % of the testosterone undecanoate in the capsule fill or composition can be present in dissolved form. In another embodiment, at least about 5 wt % of the testosterone undecanoate in the capsule fill or composition can be present in undissolved form.

The oral dosage capsules of the present application can include dosages of testosterone undecanoate of at least 50 mg. The oral dosage capsules of the present application can include dosages of testosterone undecanoate of about 80 mg to about 400 mg. In another embodiment, the oral dosage capsule can include about 80 mg to about 140 mg testosterone undecanoate. In another embodiment, the oral dosage capsule can include about 120 mg to about 300 mg testosterone undecanoate. In yet a further embodiment, the oral dosage capsule can include about 150 mg to about 250 mg of testosterone undecanoate. With this in mind, the compositions and oral dosage capsule can be used as part of dosing regimens to provide daily doses of about 250 mg to about 650 mg per day, preferably, daily doses of about 350 mg to about 650 mg per day The solubilizers used in the pharmaceutical compositions and oral dosage capsules of the present invention play role in the ability of the formulation to provide the desired therapeutic characteristics. Solubilizers that can be used can be selected from a variety of compounds and mixtures of compounds that have the ability to facilitate loading of testosterone undecanoate. The solubilizer can comprise about 50 wt % to about 86 wt % of the composition or capsule fill. In one embodiment, the solubilizer can comprise about 55 wt % to about 82 wt % of the pharmaceutical composition or oral dosage capsule. In another embodiment, the solubilizer can comprise about 60 wt % to about 80 wt % of the pharmaceutical composition or oral dosage capsule. In one embodiment, the solubilizer can be such that the testosterone undecanoate can have solubility in the solubilizer, at about 37° C., of about 250 mg/g to about 750 mg/g (mg testosterone undecanoate/gram of solubilizer and testosterone undecanoate).

Non-limiting examples of solubilizers that can be used include $C_8$ to $C_{22}$ fatty acid glycerides, omega fatty acids, and mixtures thereof. In one embodiment, the $C_8$ to $C_{22}$ fatty acid glycerides can include $C_8$ to $C_{22}$ medium and/or long chain monoglycerides, medium and/or long chain diglycerides, or mixtures of a mixture of medium and/or long chain monoglycerides and medium and/or long chain diglycerides. In another embodiment, the solubilizer can consist essentially of medium and/or long chain monoglycerides and/or diglycerides. Medium to long chain monoglycerides and diglycerides refers to compounds having chain lengths of $C_8$ to $C_{22}$. In one embodiment, the mixture of monoglycerides and diglycerides can have chain lengths of $C_8$ to about $C_{13}$. In another embodiment, the mixture of monoglycerides and diglycerides can have chain lengths of about $C_{14}$ to about $C_{22}$. When the solubilizer includes $C_8$ to $C_{22}$ fatty acid glycerides, monoglycerides can comprise at least about 40 wt % of the $C_8$ to $C_{22}$ fatty acid glycerides (such as commercially available Maisine® 35-1, Capmul® MCM, Peceol,® and the like). In another embodiment, the monoglycerides can comprise at least about 60 wt % of the $C_8$ to $C_{22}$ fatty acid glycerides. In yet a further embodiment, the monoglycerides can comprise at least about 80 wt % of the $C_8$ to $C_{22}$ fatty acid glycerides.

Non-limiting examples of $C_8$ to $C_{22}$ fatty acid glycerides that can be used as solubilizers in pharmaceutical compositions and oral dosage capsules of the present invention include monoglycerides and/or diglycerides derived from sources such as maize oil, poppy seed oil, safflower oil, sunflower oil, borage seed oil, coconut oil, palm kernel oil, castor oil, and mixtures thereof. Although not essential, the solubilizer can also include a triglyceride. The triglyceride can be a medium and/or long chain triglyceride, or mixture thereof, and can be present alone or with other solubilizers. The triglycerides can be selected from a variety of well-known pharmaceutically acceptable triglycerides including, but not limited to vegetable oils such as peanut oil, safflower oil, sunflower oil, olive oil, castor oil, corn oil, maize oil, flax seed oil, wheat-germ oil and the like, or their hydrogenated derivatives and their mixtures thereof. Additional triglyceride sources can include animal derived oils such as fish oil, seal oil, whale oil, and the like, triglycerides of $C_8$-$C_{22}$ fatty acids or their mixtures; triglycerides of $C_8$-$C_{13}$ fatty acids; triglycerides of $C_{14}$-$C_{22}$ fatty acids. In one embodiment, the composition can include a fatty acid triglyceride and the testosterone undecanoate can comprise at least about 25 wt % of the composition. In another embodiment, the triglyceride can be castor oil. In yet a further embodiment, the castor oil can comprise about 45 wt % or less of the total composition. In yet another embodiment, the castor oil can comprise about 40 wt % or less of the solubilizer. In a further embodiment, the composition can be free of castor oil. In one embodiment of the invention, the solubilizer can include a glyceryl palmitostearate, a glyceryl stearate, a glyceryl distearate, glyceryl monostearate, or a combination thereof.

In another aspect of the invention, the solubilizer can include a $C_8$ to $C_{22}$ fatty acid glycerides that is monoglycerides and/or diglycerides of capric acid, caprylic acid, or mixtures thereof. In another embodiment, the solubilizer can include a $C_8$ to $C_{22}$ fatty acid glycerides that is a monoglycerides and/or diglycerides of linoleic acid, oleic acid, or mixtures thereof. Other examples of $C_8$ to $C_{22}$ fatty acids that can be used include capric acid, pelargonic acid, caprylic acid, undecanoic acid, lauric acid, myristic acid, palmitic acid, stearic acid, oleic acid, linoleic acid, linolenic acid, arachodonic acid, eicosapentaenoic acid, docosahexanoic acid, and mixtures thereof. In one embodiment, the $C_8$ to $C_{22}$ fatty acid can be capric acid, caprylic acid, undecanoic acid, lauric acid, myristic acid, palmitic acid, stearic acid, oleic acid, linoleic acid, linolenic acid or mixtures thereof. In another embodiment, the $C_8$ to $C_{22}$ fatty acid can be selected from the group consisting of capric acid, caprylic acid, oleic acid, linoleic acid, and mixtures thereof. In one embodiment, the composition or capsule fill can be free of ionizable fatty acids. In another embodiment, the composition or capsule fill can be free of oleic acid.

In a further embodiment, the solubilizer can include an alcohol. Non-limiting examples of alcohols that can be used as solubilizers include tocopherol, ethyl alcohol, isopropanol, butanol, benzyl alcohol, ethylene glycol, propylene glycol, butanediol, glycerol, pentaerythritol, transcutol, dimethyl isosorbide, polyethylene glycol and mixtures thereof. In one embodiment, the solubilizer can be ethyl alcohol, benzyl alcohol, tocopherol, and mixtures thereof.

The pharmaceutical compositions and oral dosage capsules can also include a dispersant. In one aspect of the invention, the dispersant can be a hydrophilic surfactant having an HLB value of greater than 10, a lipophilic surfactant having an HLB value of 10 or less, or combinations thereof. In one embodiment, the compositions and oral dosage forms can include at least one hydrophilic surfactant. In another embodiment the capsule fill includes at least one hydrophilic surfactant and at least one lipophilic surfactant.

Unlike dosage forms containing ionizable components such as fatty acids (e.g. oleic acid), which are prone to being ionized at higher pH values thereby becoming charged and serving as a hydrophilic surfactant, it has been found that for improved bioavailability or activity of TU for testosterone therapy it can be useful for a composition's performance to be robust with regards to inter-conversion between hydrophilic and hydrophobic species as determined by the absence of ionized ionizable fatty acid due to pH changes such as encountered in the gastro-intestinal tract.

The total amount of lipophilic component is the total amount in wt % of the lipophilic components including the mono-, di- and/or tri-glycerides and the lipophilic surfactants, if present in the composition. In one embodiment, the lipophilic surfactant includes the solubilizer and the lipophilic surfactant. The total amount of hydrophilic surfactant is the total amount (in wt %) of the added hydrophilic surfactant and that hydrophilic surfactant formed in situ in an aqueous medium as a function of pH (e.g. intestinal pH) due to the hydrophilic ionized ionizable fatty acid (e.g. oleate) formed from lipophilic unionized ionizable fatty acid (oleic acid).

Therefore, even though fatty acid such as oleic acid may be a good solubilizer for testosterone undecanoate, its bioavailability and activity is substantially compromised with fatty acid containing compositions either by being unable to continue to solubilize the drug, or be inadequate facilitator for chylomicron related testosterone undecanoate absorption or can be slow to allow drug to partitioning out of the carrier.

When present, the hydrophilic surfactant can, but does not have to have appreciable solubilizing effect for the testosterone undecanoate present in the composition. Non-limiting examples of hydrophilic surfactants that can be included are non-ionic hydrophilic surfactants such as polysorbates, polyoxyethylene hydrogenated vegetable oils, polyoxyethylene vegetable oils; polyoxyethylene sorbitan fatty acid esters; polyoxyethylene-polyoxypropylene block copolymers; polyglycerol fatty acid esters; polyoxyethylene glycerides; polyoxyethylene sterols, derivatives and analogues thereof; reaction mixtures of polyols and at least one member of the group consisting of fatty acids, glycerides, vegetable oils, hydrogenated vegetable oils, fractionated oils and sterols; tocopheryl polyethylene glycol succinates; sugar esters; sugar ethers; sucroglycerides; mixtures thereof; alkylglucosides; alkylmaltosides; alkylthioglucosides; lauryl macrogolglycerides; polyoxyethylene alkyl ethers; polyoxyethylene alkylphenols; polyethylene glycol fatty acids esters; polyethylene glycol glycerol fatty acid esters; polyoxyethylene sorbitan fatty acid esters; polyoxyethylene-polyoxypropylene block copolymers such as poloxamer—108, 188, 217, 238, 288, 338, 407, 124, 182, 183, 212, 331, or 335, or combinations thereof; ionic hydrophilic surfactants such as sodium dodecyl sulphate, docusate sodium; bile acid, cholic acid, deoxycholic acid, chenodeoxycholic acid, salts thereof, and mixtures thereof. In one embodiment, the pharmaceutical composition or oral dosage form can be substantially free of hydrophilic surfactants.

In one embodiment, the hydrophilic surfactant can have at least one characteristic of: 1) being present in an amount such that it does not appreciably solubilize testosterone undecanoate present in the composition; or 2) the solubility of testosterone undecanoate in the hydrophilic surfactant at about 25° C., is less than 100 mg/gram or less, based on the total weight of the testosterone undecanoate and the solubilizer.

In one embodiment, the hydrophilic surfactant can have at least one characteristic of: 1) being present in an amount such that it solubilizes less than 5 wt % of the testosterone undecanoate present in the composition; or 2) the solubility of testosterone undecanoate in the hydrophilic surfactant at about 25° C., is less than 100 mg/gram or less, based on the total weight of the testosterone undecanoate and the surfactant. In another embodiment, the hydrophilic surfactant can have at least one characteristic of: 1) the hydrophilic surfactant is present in an amount such that it solubilizes less than 5 wt % of the testosterone undecanoate present in the composition; or 2) the solubility of testosterone undecanoate in the hydrophilic surfactant at about 25° C., is about 50 mg/gram or less, based on the total weight of the testosterone undecanoate and the surfactant. In yet a further embodiment, the hydrophilic surfactant can have at least one characteristic of: 1) the hydrophilic surfactant is present in an amount such that it solubilizes less than 5 wt % of the testosterone undecanoate present in the composition; or 2) the solubility of testosterone undecanoate in the hydrophilic surfactant at about 25° C., is about 50 mg/gram or less, based on the total weight of the testosterone undecanoate and the surfactant. In yet a further embodiment, the hydrophilic surfactant can have the characteristic of: 1) the hydrophilic surfactant is present in an amount such that it solubilizes less than 5 wt % of the testosterone undecanoate present in the composition; and 2) the solubility of testosterone undecanoate in the hydrophilic surfactant at about 25° C., is about 50 mg/gram or less, based on the total weight of the testosterone undecanoate and the surfactant.

As discussed above, in some embodiments the compositions and oral dosage capsules can include at least one lipophilic surfactant. Various lipophilic surfactants can be used including, but not limited to reaction mixtures of alcohols or polyalcohols with a variety of natural and/or hydrogenated oils such as PEG-5 hydrogenated castor oil, PEG-7 hydrogenated castor oil, PEG-9 hydrogenated castor oil, PEG-6 corn oil (Labrafil® M 2125 CS), PEG-6 almond oil (Labrafil®M 1966 CS), PEG-6 apricot kernel oil (Labrafil®M 1944 CS), PEG-6 olive oil (Labrafil®M 1980 CS), PEG-6 peanut oil (Labrafil®M 1969 CS), PEG-6 hydrogenated palm kernel oil (Labrafil®. M 2130 BS), PEG-6 palm kernel oil (Labrafil® M 2130 CS), PEG-6 triolein (Labrafil® M 2735 CS), PEG-8 corn oil (Labrafil® WL 2609 BS), PEG-20 corn glycerides (Crovol® M40), PEG-20 almond glycerides (Crovol® A40), lipophilic polyoxyethylene-polyoxypropylene block co-polymers (Pluronic® L92, L101, L121 etc.); propylene glycol fatty acid esters, such as propylene glycol monolaurate (Lauroglycol FCC), propylene glycol ricinoleate (Propymuls), propylene glycol monooleate (Myverol P-06), propylene glycol dicaprylate/dicaprate (Captex® 200), and propylene glycol dioctanoate (Captex® 800), propylene glycol mono-caprylate (Capryol® 90); propylene glycol oleate (Lutrol OP2000); propylene glycol myristate; propylene glycol mono stearate; propylene glycol hydroxy stearate; propylene glycol ricinoleate; propylene glycol isostearate; propylene glycol mono-oleate; propylene glycol dicaprylate/dicaprate; propylene glycol dioctanoate; propylene glycol caprylate-caprate; propylene glycol dilaurate; propylene glycol distearate; propylene glycol dicaprylate; propylene glycol dicaprate; mixtures of propylene glycol esters and glycerol esters such as mixtures composed of the oleic acid esters of propylene glycol and glycerol (Arlacel® 186); sterol and sterol derivatives such as cholesterol, sitosterol, phytosterol, PEG-5 soya sterol, PEG-10 soya sterol, PEG-20 soya sterol, and the like;glyceryl palmitostearate, glyceryl stearate, glyceryl distearate, glyceryl monostearate, or a combination thereof; sorbitan fatty acid esters such as sorbitan monolaurate (Arlacel 20), sorbitan monopalmitate (Span-40), sorbitan monooleate (Span-80), sorbitan monostearate, and sorbitan tristearate, sorbitan monolaurate, sorbitan monopalmitate, sorbitan monooleate, sorbitan trioleate, sorbitan sesquioleate, sorbitan tristearate, sorbitan monoisostearate, sorbitan sesquistearate, and the like; and mixtures thereof. It is important to note that some lipophilic surfactants may also function as the solubilizer component of the compositions and oral dosage forms.

In one embodiment, the lipophilic surfactant can be selected from the group consisting of propylene glycol mono caprylate, propylene glycol oleate, propylene glycol monostearate, propylene glycol monolaurate, propylene glycol mono-oleate, propylene glycol dicaprylate/dicaprate, sorbitan monooleate, PEG-5 hydrogenated castor oil, PEG-7 hydrogenated castor oil, PEG-9 hydrogenated castor oil, PEG-6 corn oil, PEG-6 almond oil, PEG-6 apricot kernel oil, PEG-6 olive oil, PEG-6 peanut oil, PEG-6 hydrogenated palm kernel oil, sorbitan monolaurate (Arlacel 20), sorbitan monopalmitate, sorbitan monooleate, sorbitan monostearate, sorbitan tristearate, sorbitan monolaurate, sorbitan monopalmitate, sorbitan monooleate, sorbitan trioleate, sorbitan sesquioleate, sorbitan tristearate, sorbitan monoisostearate, and combinations thereof.

In another aspect of the invention, the pharmaceutical compositions and/or oral dosage capsules, namely the capsule fill, can include a solidifying agent. As defined above, a solidifying agent is a pharmaceutically acceptable additive that is in a solid physical state at 20° C. Typically solidifying agents facilitate the solidification of the pharmaceutical compositions of the present invention at temperatures around room temperature. The compositions and capsule fill of the present invention, including those with solidifying agents, can be non-liquid at standard temperature and pressure. In one embodiment, the composition and capsule fill can be semi-solid at standard temperature and pressure. In yet another embodiment, the composition and capsule fill can be solid at standard temperature and pressure. When present, the solidifying agent can comprise from about 0.1 wt % to about 25 wt % of the pharmaceutical composition or oral dosage capsule. In another embodiment, the solidifying agent can comprise about 2 wt % to about 20 wt % of the composition or oral dosage capsule. In yet a further embodiment, the solidifying agent can comprise about 3 wt % to about 15 wt % of the composition or oral dosage capsule. In still a further embodiment, the solidifying agent can comprise about 3 wt % to about 9 wt % of the capsule fill. In yet a further embodiment, the solidifying agent can comprise 6 wt % to 9 wt % of the capsule fill. In one embodiment, the solidifying agent can melt at a temperature of about 45° C. to about 75° C. Non-limiting examples of solidifying agents that can be used include polyethylene glycols; sorbitol; gelatin; stearic acid; cetyl alcohol; cetosterayl alcohol; paraffin wax; polyvinyl alcohol; glyceryl stearates; glyceryl distearate; glyceryl monostearate; glyceryl palmitostearate; glyceryl behenate; waxes; hydrogenated castor oil; hydrogenated vegetable oil; bees wax, microcrystalline wax; sterols; phytosterols; cholesterol and mixtures thereof. In one embodiment, the solidifying agent includes a polyethylene glycol (PEG) having molecular weight from about 1000 to about 20,000 and their mixtures. In another embodiment the solidifying agent includes one or more selected from the group consisting of polyethylene glycol; gelatin; stearic acid; polyvinyl alcohol; glyceryl stearates; glyceryl distearate; glyceryl monostearate; glyceryl palmitostearate; hydrogenated castor oil; hydrogenated vegetable oil and cholesterol. In one embodiment, the pharmaceutical composition can be a solid at about 20° C. In yet a further embodiment, the solubilized solid and/or the undissolved crystalline testosterone undecanoate can act as a solidifying agent.

The oral compositions of the present invention can be formulated to take any dosage form commonly known in the pharmaceutical arts such as granules, tablet or capsule. In one embodiment, the oral dosage form can be a capsule having a pharmaceutical composition of the present invention disposed therein. Both soft and hard gelatin and non-gelatin capsules can be used. The capsule size can be any size known in the art and can vary depending on the desired dosage amount. In one embodiment, the capsule can be a hard gelatin capsule having a fill volume of about 0.3 mL to about 1.1 mL. The oral dosage capsules can be immediate release, extended release, targeted release, enteric release, delayed release dosage form or combinations thereof. In a specific embodiment, the oral dosage capsule can be a delayed release dosage form. In one embodiment, the capsule can have a ratio of the amount of testosterone undecanoate to the volume of the capsule fill can be about 80 mg/mL to about 750 g/mL. In another embodiment, the capsule can have a ratio of the amount of testosterone undecanoate to the volume of the capsule fill can be about 160 mg/mL to about 375 mg/mL.

The oral dosage capsules of the present invention can be formulated such that they have distinctive release profiles. In one embodiment, an oral dosage capsule can provide in vitro release of at least about 75 wt % of the testosterone undecanoate during the first 120 minutes when tested using about 1000 mL of 8% w/v Triton X-100 in water maintained at about 37±1° C. taken in a USP-Type II dissolution apparatus set at 100 rpm. In another embodiment, the oral dosage capsule can have an in vitro release profile such that 85 wt % or less of the testosterone undecanoate is released in the first 30 minutes, when measured using about 1000 mL of 8% w/v Triton X-100 in water maintained at about 37±1° C. taken in a USP-Type II dissolution apparatus set at 100 rpm. In further embodiment, the oral dosage capsule can have an in vitro release profile such that 70 wt % or less of the testosterone undecanoate is released in the first 30 minutes, when measured using about 1000 mL of 8% w/v Triton X-100 in water maintained at about 37±1° C. taken in a USP-Type II dissolution apparatus set at 100 rpm. In an additional embodiment, the oral dosage capsule can have a in vitro release profile such that at least 35 wt % of the testosterone undecanoate is released in the first 30 minutes, when measured using about 1000 mL of 8% w/v Triton X-100 in water maintained at about 37±1° C. taken in a USP-Type II dissolution apparatus set at 100 rpm. In still an additional embodiment, the oral dosage capsule can have an in vitro release profile such that at least 40 wt % of the testosterone undecanoate is released in the first 30 minutes, when measured using about 1000 mL of 8% w/v Triton X-100 in water maintained at about 37±1° C. taken in a USP-Type II dissolution apparatus set at 100 rpm.

In one aspect, the dosage form can comprise two or more of populations of testosterone undecanoate compositions of the present invention. In one embodiment, at least one of the populations can be formulated to start releasing testosterone undecanoate immediately into a surrounding aqueous medium. In another embodiment, at least one the populations can be formulated to start releasing testosterone undecanoate after at least 2 hours. In another embodiment, at least one the populations can be formulated to release testosterone undecanoate after about 4 hours, or after about 6 hours, or after about 8 hours, or after about 10 hours.

In yet a further embodiment, at least one of the populations can be formulated to start releasing testosterone undecanoate immediately after oral administration to a human. In one particular case, at least one of the populations can be formulated to start releasing testosterone undecanoate in the duodenal region after oral administration to a human. In another particular case, at least one of the populations can be formulated to start releasing testosterone undecanoate in the small intestine after oral administration to a human.

In yet a further embodiment, at least one of the populations includes a pH sensitive substance. In a particular case, at least one of the populations can be formulated to start releasing testosterone undecanoate at a pH of from about 1.0 to about 3.4. In another particular case, at least one of the populations can be formulated to start releasing testosterone undecanoate at a pH of from about 3.5 to about 5.5. In another particular case, at least one of the populations can be formulated to start releasing testosterone undecanoate at a pH of from about 5.6 to about 6.8. In another particular case, at least one of the populations can be formulated to start releasing testosterone undecanoate at a pH about 7.0 or more.

In yet another aspect, the dosage form comprising two or more of populations of testosterone undecanoate compositions of the present invention is a capsule. In a particular case, the dosage form is a capsule in capsule dosage form. In another particular case the dosage form is a tablet in capsule dosage form. In another particular case, the dosage form is a granules or pellets or tablets or minitablets disposed in a capsule.

The oral dosage capsules of the present invention can be formulated such that, when administered to a human male they provide a serum total testosterone $C_{avg}$ ranging about 300 ng/dL to about 1100 ng/dL. In another embodiment, the oral dosage capsules can be formulated such that, upon single administration to a human male, they provide a serum total testosterone $C_{avg}$ ranging about 350 ng/dL to about 800 ng/dL. In another embodiment, the oral dosage capsules can be formulated such that, upon single administration to a human male, they provide a serum total testosterone $C_{avg}$ ranging from about 400 ng/dL to about 600 ng/dL. It is noted that such $C_{avg}$ value can be achieved based on administration every 12 hours or every 8 hours. Similarly, the oral dosage capsules can be formulated such that, upon single administration to a human male, they provide a serum testosterone undecanoate $C_{avg}$ of about 1.5 ng/mL to about 1 mcg/mL. In a further embodiment, the oral dosage capsules can be formulated such that, upon single administration to a human male, they provide a serum testosterone undecanoate $C_{avg}$ of about 3 ng/mL to about 850 ng/mL. In a further embodiment, the oral dosage capsules can be formulated such that, upon single administration to a human male, they provide a serum testosterone undecanoate $C_{avg}$ of about 10 ng/mL to about 850 ng/mL. In one embodiment, upon a single dose administration of the capsule to a subject the capsule provides a dose-normalized serum testosterone $C_{max}$ of about $3 \times 10^{-6}$ $dL^{-1}$ or higher. In another embodiment, upon a single dose administration of the capsule to a subject the capsule provides a dose-normalized serum testosterone $C_{avg}$ of about $1.9 \times 10^{-6}$ $dL^{-1}$ or higher. In yet another embodiment, upon a single dose administration of the capsule to a subject the capsule provides a dose-normalized serum testosterone $C_{avg}$ of about $2.7 \times 10^{-6}$ $dL^{-1}$ or higher.

In another aspect, the oral dosage capsules can be formulated such that upon single administration d to a male human subject they provide a ratio of serum testosterone undecanoate $C_{avg}$ to serum total testosterone $C_{avg}$ of about 4:1 to about 75:1. In a further embodiment, the oral dosage capsules can be formulated such that, upon single administration to a human male, they provide a ratio of serum testosterone undecanoate $C_{avg}$ to serum total testosterone $C_{avg}$ of about 20:1 to about 50:1. In yet another embodiment, the oral dosage capsules can be formulated such that, upon single administration to a human male, the oral dosage capsule provides a ratio of serum total testosterone $C_{avg}$ to dose of testosterone undecanoate of about $0.2 \times 10^{-6}$ $dL^{-1}$ to about $20 \times 10^{-6}$ $dL^{-1}$.

In one embodiment, a single dose of the testosterone undecanoate composition or oral dosage form can provide a serum total testosterone $C_{avg}$ of about 300 ng/dL or more from about 0.5 hours to about 24 hours after oral administration with a meal or a snack. In a further embodiment, a single dose of a testosterone undecanoate composition or oral dosage capsule can provide a serum total testosterone $C_{avg}$ of about 300 ng/dL or more at about 20 hours after oral administration with a meal or a snack. In yet a further embodiment, a single dose of the testosterone undecanoate composition can provide a serum total testosterone $C_{avg}$ of about 300 ng/dL or more at about 18 hours after oral administration with a meal or a snack. In still a further embodiment, a single dose of the testosterone undecanoate composition can provide a serum total testosterone $C_{avg}$ of about 300 ng/dL or more at about 16 hours after oral administration with a meal snack. In still a further embodiment, a single dose of the testosterone undecanoate composition can provide a serum total testosterone $C_{avg}$ of about 300 ng/dL or more at about 12 hours after administration after oral administration with a meal snack. In still a further embodiment, a single dose of the testosterone undecanoate composition can provide a serum total testosterone $C_{avg}$ of about 300 ng/dL or more at about 8 hours after oral administration with a meal or snack. The meal that is administered with the composition or oral dosage form can be a standard meal or a snack.

The compositions and oral dosage capsules disclosed herein can be, but do not have to be, orally administered with food. In one embodiment, the composition or oral dosage capsule can be administered with a meal, such as a meal that provides about 200 to about 1000 calories of energy. In another embodiment, the composition or oral dosage capsule can be administered with a standard meal. In another embodiment, the composition or oral dosage capsule can be administered with a meal that provides about 50% of the calories derived from the fat. In another embodiment, the composition or oral dosage capsule can be administered with a high-fat, high calorie meal. In another embodiment, the composition or oral dosage capsule can be administered with a meal that provides about 500 to about 1000 calories of energy. In another embodiment, the composition or oral dosage capsule can be administered with a meal that provides about 400 to about 700 calories derived from the fat therein. The compositional make-up of the meals that are administered can vary depending on the tastes and dietary needs of a subject. However, in some situations it may be beneficial to administer the compositions and oral dosage forms with meals that provide no fat or up to about 50 g of fat. In one embodiment, the meal can provide about 10 g to about 50 g of fat. In yet a further embodiment, the meal can provide about 30 g of fat. The testosterone undecanoate dosage compositions and oral dosage capsules disclosed herein can be orally administered in a 24 hours' dosing regimen (also referred to as or a daily dosing regimen) that is suitable to the needs of the subject. The 24 hours' dosing regimen can include administering the dosage forms after meals in the morning, at about noon, in the evening, at about night time or combinations thereof. The 24 hours' dosing regimen can include dosing one or more dosage units at one or more administration times. In one embodiment, the pharmaceutical composition is administered as a single oral dosage capsule.

The testosterone undecanoate compositions and oral dosage capsules can provide increased bioavailability as compared to other testosterone undecanoate compositions and dosage forms. In some embodiments, the testosterone undecanoate oral dosage capsules can provide an in vitro release of less than about 85 wt % of the testosterone undecanoate within the first 30 minutes. In another embodiment, the testosterone undecanoate oral dosage capsules can provide an in vitro release of about 90 wt % or less testosterone undecanoate within the first 30 minutes. The in vitro release is determined in about 1000 mL of 8% w/v Triton X-100 in water maintained at about 37° C. in an USP Type-2 Apparatus at about 100 rpm. It has been discovered that these testosterone undecanoate oral dosage capsules, i.e. those having the above release characteristics, provide at least a 10% increase in the testosterone undecanoate AUC after single oral dosages are administered to human males. The increase is as compared to equivalent dosages of testosterone undecanoate in an immediate release dosage forms administered under same conditions. Immediate release dosage forms are defined as being dosage forms which release more than 95 wt % of the testosterone undecanoate within the first 30 minutes using the same in vitro release conditions described above. Further, in one embodiment, the testosterone undecanoate oral dosage capsules can provide at least a 15% increase in the testosterone undecanoate AUC as compared to an immediate release dosage oral dosage form.

In another embodiment, the testosterone undecanoate oral dosage capsules disclosed herein can provide at least a 10% reduction in the inter-subject variability of the testosterone undecanoate $C_{max}$, and/or the testosterone undecanoate AUC as compared to immediate release equivalent dosage containing oral dosage forms. In another embodiment, the testosterone undecanoate oral dosage capsules disclosed herein can provide 10% or more testosterone bioavailability in subjects as compared to immediate release equivalent dosed oral dosage forms.

The pharmaceutical compositions and oral dosage capsules of the present invention can be formulated such that upon administration of one or more capsules daily to each subject in a group of at least 24 hypogonadal males for a period of at least 84 days, the capsule provides a serum testosterone $C_{avg}$ of 300 ng/dL to 1100 ng/dL in at least 75% of the hypogonadal males in the group. Additionally, under such an administration regimen the capsule can be such that at least one of the following regarding the PK parameter of the administration is true: a) a serum testosterone $C_{max}$ of less than 1500 ng/dL in at least 85% of the hypogonadal males in the group; b) a serum testosterone $C_{max}$ of about 1800 ng/dL to about 2500 ng/dL in 5% or less of the hypogonadal males in the group; or c) a serum testosterone $C_{max}$ greater than 2500 ng/dL in about 1% or less of the hypogonadal males in the group.

In one embodiment, the administration over the at least 84 days can be divided into two dosing regimens including an initial regimen in which an initial dose is administered and a maintenance regimen in which a maintenance dose is administered. In one aspect of this embodiment, the daily dose of the maintenance regimen of the testosterone undecanoate can be about 45% to about 155% of the initial daily dose. In another aspect of the embodiment, the daily dose of the maintenance regimen of the testosterone undecanoate can be about 66% to about 133% of the initial daily dose. In another aspect of the embodiment, the daily dose of the maintenance regimen of the testosterone undecanoate can be about 75% to about 125% of the initial daily dose. In yet a further aspect of this embodiment, the capsule can be formulated such that the amount of the daily dose of the maintenance regimen is based on at least one testosterone undecanoate dose titration metric derived from the measurement of the serum testosterone concentration on at least one titration node day. The titration node day can be any single day beginning on day 15 to day 84 after administration of the initial daily dose. In one embodiment, the titration node day can be any day from day 15 to day 21 after administration the daily dose of the initial regimen of the initial regimen. In yet another embodiment, the titration node day is any day from day 22 to day 30 after administration of the daily dose of the initial regimen of the initial regimen. In further embodiments, the titration node day can be any day from day 22 to day 30, from day 31 to day 63, or from day 64 to day 84 after administration of the daily dose of the initial regimen of the initial regimen.

In one aspect, the titration based on the titration metric can be such that if the testing of the metric is serum testosterone concentration and the testing is done at time (t) of 1 to less than 3 hours following administration the serum testosterone concentration is less than 12.0 ng/mL then the daily TU dose may need to be increased and if the serum testosterone concentration is more than 9.4 then the daily TU dose may need to be decreased. In another aspect, the titration metric is serum testosterone concentration and the testing is done at time (t) if at time (t) of 3 to less than 8 hours following administration the serum testosterone concentration is less than 4.1 ng/mL daily TU dose may need to be increased and if the serum testosterone concentration is more than 18.1 then the daily TU dose may need to be decreased. In another aspect, the titration metric is serum testosterone concentration and the testing is done at time (t) of 8 to less than 12 hours following administration the serum testosterone concentration is less than 3.0 ng/mL then the daily TU dose may need to be increased and if the serum testosterone concentration is more than 7.8 then the daily TU dose may need to be decreased. In yet a further aspect, the titration metric is serum testosterone concentration and the testing is done at time (t) of 12 to less than 14 hours following administration the serum testosterone concentration is less than 1.4 ng/mL then the daily TU dose may need to be increased and if the serum testosterone concentration is more than 2.9, then the daily TU dose may need to be decreased. The above titrations are only exemplary of the possible titrations that can be accomplished using the methods of the present invention. It is further noteworthy that the titrations can be used in conjunction with the methods taught herein including the disclosed methods of providing a serum concentration of testosterone within a target serum testosterone $C_{ave}$ range for a male subject.

The testosterone undecanoate compositions and oral dosage capsules disclosed herein can be used in conjunction with or as a component of a diagnostic or treatment kit that enables the diagnosis and treatment of a male patient in need of testosterone therapy. The diagnostic or treatment kit may comprise the testosterone undecanoate composition or oral dosage capsule disclosed herein along with one or more other components, including, but not limited to 1) instructions to enable those ordinarily skilled in the art to prepare a dosage form for immediate dispensing to the subject in need of; 2) one or more containers filled with one or more of the ingredients of the oral pharmaceutical dosage forms of the invention. Suitable containers include, for example, a bottle, a box, a blister card, a foil packet, or a combination thereof; 3) a tamper proof container or packaging; 4) other pharmaceutical dosage forms including other active agents including PDE-5 inhibitors and glucocorticosteroids; 5) Notice or printed instructions: in a form prescribed by a governmental agency regulating the manufacture, use, or sale of pharmaceuticals or biological products, which notice reflects approval by the agency of the manufacture, use, or sale for human administration to treat a condition that could be treated by oral testosterone therapy; 6) A "planner" for monitoring and tracking administration of the oral dosage forms; 7) Containers for storing and transporting the components of the kit; 8) total testosterone or free testosterone testing kits; 9) Sex Hormone binding globulin, SHBG, testing kits; 10) Body mass index testing materials to identify high risk patients; 11) tests for identifying patients with hypogonadism; 12) tests to assess testicular function or impotency; 13) test for bone mineral density/osteoporosis; 14) test for hair density 15) test for muscle mass and strength; 16) test for determining erectile dysfunction; 17) test for decreased libido; 18) test for fatigue, depression, mood disorders or irritability; 19) test for infertility; 20) test for prostate condition.

The oral dosage compositions and oral dosage capsules disclosed herein can be co-administered with other active agents in order to treat a target condition. One or more co-administered active agents can be admixed with the testosterone undecanoate containing compositions and/or oral dosage forms of the current invention. For example, phosphodiesterase type 5 (PDE-5) inhibitors, such as sildenafil citrate, tadalafil, vardenafil, avanafil, lodenafil, mirodenafil, udenafil, and the like, are used to block the degradative action of phosphodiesterase type 5 enzyme on cyclic GMP in the smooth muscle cells lining the blood vessels supplying the corpus cavernosum of the penis and are frequently used to treat erectile dysfunction. Such compounds could be co-administered with the compositions and oral dosage forms of the present invention in order to provide improved clinical outcomes through synergistic pharmacological action as measured by improved (sooner, better and longer lasting) erection, potency, libido, mood, body mass, etc. in males relative to administration of the testosterone or the co-administered PDE-5 alone. The testosterone undecanoate compositions and oral dosage capsules can also be co-administered with one or more other active agents such as aromatase inhibitors (for example letrozole, anastrozole, exemestane, fadrozole, vorozole, formestane etc.), dopamine agonists (for example apomorphine, bromocriptine, cabergoline, pergolide, ropinirole, rotigotine, pramipexole, fenoldopam etc.), prostaglandins (for example alprostadil), alpha blockers (for example yohimbine, phentolamine),vasodilators (for example minoxidil) and the like, for improved clinical outcomes through synergistic pharmacological action as measured by improvements in one or more of the secondary sexual characteristics in males such as sexual activity, potency, libido, erection etc., mood, body mass and the like, relative to administration of either the testosterone or the co-administered active agent alone.

In another aspect, the subjects receiving the dosage form of this invention are expected to improve in quality of life. The patient reported outcome may be employed to measure the improvement in other levels apart from primary (serum testosterone $C_{ave}$) and secondary (serum testosterone $C_{max}$, $C_{min}$, $C_{trough}$, etc) outcomes which are typically quantified by the PK profiles. For measuring the pharmacodynamic related efficacy outcomes, the improvements in the symptoms are usually monitored by ranking or scoring, dairy recording etc, by the subject being treated and/or the partner or spouse of the subject, in a timely manner before and during the therapy.

Accordingly, in one embodiment the dosage forms and the methods of current invention improve sexual symptoms including but not limited to sexual activity engagement, sexual thoughts or fantasies; feel of sexual desire; frequency of experience of morning erections; maintaining erections as long as desired; hardness of erection; ejaculation; enjoyment/satisfaction of sexual activity. In another embodiment the dosage form and the methods of current invention improves or enhances the physical and physiological symptoms and body energy level as assessed by the level of happiness with the body looks; body muscle mass, body weight and weakness/strength of muscles; level of tiredness; level of physical tiredness; level of energy; level of exhaustion and the like.

In another embodiment the dosage form and the methods of the current invention improves the symptoms related to the sleep symptoms and memory/cognition as assessed by quality of sleep at night; frequency of sleep restfulness; number of wake-up times during the night; frequency of feeling of satisfactory rest, frequency of accidental doze off during the day; frequency of purposely taken naps during the day; focus attention to tasks; level of forgetfulness; desire or ambition to take on new projects; short attention span; successful/efficient completion of tasks.

In a further aspect, the compositions of the current invention can be formulated to provide a gastro-retentive dosage form. In one embodiment, the gastro-retentive dosage form is a capsule. In another embodiment, the gastro-retentive dosage form is retained in the upper gastro-intestinal tract for at least one hour post-dosing. In another embodiment, the gastro-retentive dosage form is retained in the upper gastro-intestinal tract for at least two hours post-dosing. In another embodiment, the gastro-retentive dosage form is retained in the upper gastro-intestinal tract for at least 4 hours post-dosing. In another embodiment, the gastro-retentive dosage form is formulated to float in the stomach after dosing. In another embodiment, the gastro-retentive dosage form is formulated to expand when it comes in contact with aqueous medium to at least 1.3 times its size compared to its size when it is not in contact with the aqueous use environment. In another embodiment, the gastro-retentive dosage form is formulated to adhere to the lining of the stomach wall after dosing.

The compositions and the oral dosage capsules of the current invention can also include one or more of other additives selected from binders, bufferants, diluents, disintegrants, flavors, colorants, taste-masking agents, resins, pH modifiers, lubricants, glidants, thickening agent, opacifying agent, humectants, desiccants, effervescing agents, plasticizing agents and the like.

In addition to the compositions and oral dosage capsules of the present invention, a method for providing a serum concentration of testosterone within a target serum testosterone concentration $C_{ave}$ range for a male subject is also provided. It is noted that the compositions and oral dosage capsules of the present invention can be used in the conjunction with this method and that the teachings regarding the compositions and their administration provided above can be applied and used in connection with the methods disclosed here. The method includes the step of orally administering to the male subject an initial regimen including a daily dose of a testosterone undecanoate-containing composition. The testosterone undecanoate comprises about 14 wt % to about 35 wt % of the testosterone undecanoate-containing composition and the daily dose provides about 350 mg to about 650 mg of testosterone undecanoate to the male subject. After the initial regimen, the method includes a step of determining a dose titration metric based on a measurement of serum testosterone concentration for the male subject on at least one titration node day within the initial regimen. The method further includes the step of orally administering to the male subject a maintenance regimen including a daily dose of testosterone undecanoate-containing composition that comprises about 14 wt % to about 35 wt % of the testosterone undecanoate. The maintenance regimen provides a daily dose of testosterone undecanoate to the subject based on the titration metric determined on the at least one titration node day of the initial regimen and is sufficient to provide a serum testosterone plasma concentration that is closer to or within the target range.

In one embodiment, the method for providing a serum concentration of testosterone within a target serum testosterone concentration $C_{ave}$ range for a male subject can further include the steps of determining a dose titration metric based on a measurement of serum testosterone concentration for the male subject on at least one titration node day within the maintenance regimen. Following the determination of the titration metric the method includes the step of orally administering to the male subject a second maintenance regimen including a daily dose of testosterone undecanoate-containing composition, wherein the testosterone undecanoate-containing composition comprises about 14 wt % to about 35 wt % of the testosterone undecanoate-containing composition. The second maintenance regimen provides a daily dose of testosterone undecanoate to the subject based on the titration metric determined on the at least one titration node day of the maintenance regimen sufficient to provide a serum testosterone plasma concentration within the target range. Following the second maintenance regimen, the steps of determining the titration metric and administering an additional maintenance regimen can be repeated as needed in order to achieve the a serum testosterone concentration within the target range.

In the above method, the daily dose administered in the initial regimen can be the same dosage amount as the daily dose administered in the maintenance regimen. In one embodiment, the daily dose of the maintenance regimen can provide an amount of testosterone undecanoate that is about 45% to about 155% of that of the initial daily dose. In another embodiment, the daily dose of the maintenance regimen can provide an amount of testosterone undecanoate that is about 66% to about 133% of that of the daily dose in the initial regimen. In yet another embodiment, the daily dose of the maintenance regimen can provide an amount of testosterone undecanoate that is about 75% to about 125% of that of the daily dose in the initial regimen.

The determination step or steps of the above described methods can be any single day from day after day 15 of the initial regimen. In one embodiment, the titration node day can be any single day from day 15 to day 21 following the start of the initial regimen. In another embodiment, the titration node day can be any single day from day 21 to day 30 following the start of the initial regimen. In yet a further embodiment, the titration node day is any single day from day 31 to day 63 following the start of the initial regimen. In still a further embodiment, the titration node day can be any single day from day 64 to day 84 following the start of the initial regimen.

As discussed previously, subjects with whom the methods of the present invention can be used can be those in need of testosterone therapy. In one aspect, the male subject with whom the method is being used can have a serum testosterone $C_{avg}$ of less than 300 ng/dL before beginning of the initial regimen. In another aspect, the male subject can have a serum testosterone $C_{avg}$ of less than 200 ng/dL before beginning of the initial regimen. In yet another aspect, the male subject can have a serum testosterone $C_{avg}$ of less than 300 ng/dL before beginning of the maintenance regimen. In yet a further aspect, the male subject can have a serum testosterone $C_{avg}$ of less than 200 ng/dL before beginning of the maintenance regimen. Similarly, the target serum testosterone $C_{ave}$ range can vary depending on the subject and his particular needs and physiological parameters. In one embodiment, the target serum testosterone $C_{ave}$ range can be about 300 ng/dL to 1100 ng/dL and is achieved by the method on or after day 84 following the start of the initial regimen. In another embodiment, the target serum testosterone $C_{ave}$ range can be about 300 ng/dL to about 1100 ng/dL and is achieved by the method on or after day 120 following the start of the initial regimen. In yet a further embodiment, the target serum testosterone $C_{ave}$ range can be about 300 ng/dL to about 1100 ng/dL and can be achieved by the method on or after day 180 following the start of the initial regimen.

The above described method can provide desirable pharmacokinetic parameters based on administration to a group of subjects. In one embodiment, the method of the present invention can be such that the method can provide a serum testosterone $C_{avg}$ in the range of 300 ng/dL to 1100 ng/dL in 75% or more of hypogonadal males after 84 days from the start of the initial regimen, based on a minimum group size of 24 hypogonadal males. In another embodiment, the method can provide a serum testosterone $C_{max}$ of 1500 ng/dL or less in less than or equal to 85% of hypogonadal males based on a minimum group size of 24 hypogonadal males. In yet a further embodiment, the method provides a serum testosterone $C_{max}$ in the range of 1800 ng/dL to 2500 ng/dL in about 5% or less of hypogonadal males after 84 days from the start of the initial regimen based on a minimum group size of 24 hypogonadal males. In yet a further embodiment, the method can provide a serum testosterone $C_{max}$ of 2500 ng/dL in about 1% or less of hypogonadal males after 84 days from the start of the initial regimen based on a minimum group size of 24 hypogonadal males. In one embodiment, the method can provide a steady state ratio of serum testosterone $C_{max}$ to $C_{ave}$ of 2.7 or less based on single subject administration.

The above disclosed methods provide for initial and maintenance regimens that include daily dose amounts that can be provided as twice-a-day administrations or divided into multi-dosage administrations. When a multi-dosage administration is utilized to provide the daily dose amount of testosterone undecanoate the dosages can be equal or unequal and can be administered with or without meals, depending of the designated regimen. In one aspect, when the dosages, whether twice-a-day or multi-time dosages, are administered with a meal or a snack the meal or snack can include about 15 g to about 60 g of fat. In one embodiment, the method provides for administration of the daily dose during the maintenance regimen as including twice-a-day administration of the testosterone undecanoate-containing composition in conjunction with meals. In one embodiment, the meal administered with the testosterone undecanoate-containing composition can have a total calorie content of about 350 and 1200 K calories with about 30% to about 60% of the calories in the meal being derived from fat. In another embodiment, the method can provide, at steady state, a dose-normalized serum testosterone $C_{max}$ of about $3 \times 10^{-6}$ dL$^{-1}$ or higher when administered to a male subject with meals daily in two divided doses.

EXAMPLES

The following examples are provided to promote a more clear understanding of certain embodiments of the present invention, and are in no way meant as a limitation thereon.

Example 1

Testosterone Undecanoate Composition

A testosterone undecanoate containing composition was prepared by using the components set forth in Table I. The composition is prepared by weighing all of the components, except the testosterone undecanoate, into a clean stainless steel container and mixed together at about 50° C. to about 70° C., using a stirrer. The testosterone undecanoate (TU) is added and stirred into the mixture of other components until the testosterone undecanoate dissolves. A predetermined quantity of this fill material is disposed into a capsule (for example, hard gelatin capsule) to get the required testosterone undecanoate dose per dosage unit. The capsules are allowed to cool at room temperature, banded (if required) and packaged in a HDPE bottle and tightly closed with an appropriate lid.

TABLE I

| Example 1 | Composition mg/capsule |
|---|---|
| Testosterone Undecanoate | 200 |
| Solubilizer (e.g. Glycerides of coconut oil; Capmul ® MCM) | 725 |
| Dispersant (e.g. lauroglycol) | 300 |
| Dispersant (polyoxyl 40 hydrogenated castor oil or Cremophor ® RH40) | 50 |

TU- loading (wt %) of capsule fill = 15.7%

Example 2

Testosterone Undecanoate Composition

A testosterone undecanoate containing composition was prepared similarly to the method described in Example 1 using the components set forth in Table II.

TABLE II

| Example 2 | Composition mg/capsule |
|---|---|
| Testosterone Undecanoate | 225 |
| Solubilizer (e.g. Maize oil glyceride) | 260 |
| Dispersant (e.g. lauroglycol) | 665 |

TU- loading (wt %) of capsule fill ~19.6%

Examples 3 & 4

Testosterone Undecanoate Composition

Testosterone undecanoate containing composition were prepared similarly to the method described in Example 1 using the components set forth in Tables III and IV

TABLE III

| Example 3 | Composition mg/capsule |
|---|---|
| Testosterone Undecanoate | 200 |
| Solubilizer (e.g. Glycerides of coconut oil; Capmul ® MCM) | 600 |

TU- loading (wt %) of capsule fill = 25%

TABLE IV

| Example 4 | Composition mg/capsule |
|---|---|
| Testosterone Undecanoate | 180 |
| Solubilizer (Maize oil glyceride, Maisine 35-1) | 600 |

TU- loading (wt %) of capsule fill = 23%

Example 5

Testosterone Undecanoate Composition

A testosterone undecanoate containing composition was prepared similarly to the method described in Example 1 using the components set forth in Table V

TABLE V

| Example 5 | Composition mg/capsule |
|---|---|
| Testosterone Undecanoate | 240 |
| Solubilizer (e.g. Glycerides of coconut oil; Capmul ® MCM) | 200 |
| Solubilizer (e.g. α-tocopherol) | 490 |
| Dispersant (for e.g. polyoxyl castor oil or Cremophor ® EL) | 100 |

TU- Loading per caps TU- loading (wt %) of capsule fill = 23.3%

Example 6

Testosterone Undecanoate Composition

A testosterone undecanoate containing composition was prepared by using the components set forth in Table VI and a method similar to that described in Example 1.

TABLE VI

| Example 6 | Composition mg/capsule |
|---|---|
| Testosterone Undecanoate | 200 |
| Solubilizer (e.g. Maize oil glycerides) | 490 |
| Dispersant (e.g. polysorbate 80) | 25 |
| Solidifying agent (e.g. polyethylene glycol, 8000 or PEG 8000) | 45 |

TU- Loading per capsule = 26.3%

Example 7

Testosterone Undecanoate Composition

A testosterone undecanoate containing composition was prepared by using the components set forth in Table VII and a method similar to that described in Example 1.

TABLE VII

| Example 7 | Composition mg/capsule |
|---|---|
| Testosterone Undecanoate | 240 |
| Solubilizer (e.g. Maize oil glycerides) | 325 |
| Solubilizer (e.g. oleic acid) | 125 |
| Solubilizer (e.g. Benzyl Alcohol) | 50 |
| Solubilizer (e.g. α-tocopherol) | 75 |
| Solidifying agent (e.g. PEG 8000) | 45 |

TU- Loading per capsule = 28%

Example 8

Testosterone Undecanoate Composition

A testosterone undecanoate containing composition was prepared by using the components set forth in Table VIII and a method similar to that described in Example 1.

TABLE VIII

| Example 6 | Composition mg/capsule |
|---|---|
| Testosterone Undecanoate | 240 |
| Solubilizer (e.g. oleic acid) | 400 |
| Solidifying agent—(e.g. PEG 8000) | 45 |

TU- loading (wt %) of capsule fill = 35%

Example 9

Testosterone Undecanoate Composition

A testosterone undecanoate containing composition was prepared using the components set forth in Table IX and a method similar to that described in Example 1.

TABLE IX

| Example 7 | Composition mg/capsule |
|---|---|
| Testosterone Undecanoate | 240 |
| Solubilizer (e.g. Maize oil glycerides) | 400 |
| Solubilizer (e.g. α-tocopherol) | 24 |
| Solidifying agent—(e.g. Glyceryl distearate; Percirol ® ATO 5) | 25 |

TU- loading (wt %) of capsule fill = 34.8%

Example 10

Testosterone Undecanoate Composition

A testosterone undecanoate containing composition can be prepared by using the components set forth in Table X by a method as follows: The required quantity of the glyceryl distearate or glyceryl monostearate and the PEG 8000 are placed in a stainless steel container and heated to about 50 to 70° C. to get a molten mixture. The testosterone undecanoate is added and stirred till it completely dissolves. A predetermined weight of the molten mixture is disposed into capsules and allowed to congeal at room temperature, banded and packed.

TABLE X

| Example 10 | Composition mg/capsule |
|---|---|
| Testosterone Undecanoate | 100 |
| Glyceryl distearate (Percirol ® ATO 5) or glyceryl monostearate | 200 |
| PEG 8000 | 50 |

The oral dosage capsules of Example 10, which contains non-dissolved TU, can provide, upon single administration along with food to a human male, a testosterone undecanoate AUC that is about 20% higher as compared to a composition that does not include the glyceryl distearate (Percirol® ATO 5) or glyceryl monostearate.

The composition of Example 10 can also be optionally modified so that a dispersant such as a disintegrating agent (e.g. Crospovidone at about 150 mg for every 100 mg TU dose) can be uniformly suspended under stirring in the molten testosterone undecanoate solution. This suspension can be further allowed to cooled and passed through ASTM 30 mesh get granulates or particulates which can be either filled in a capsule or compressed to a tablet.

Example 11

Testosterone Undecanoate Composition

A testosterone undecanoate containing composition wherein at least 50% of the testosterone undecanoate is dissolved is prepared by using the components set forth in Table XI and a method similar to that described under Example 1.

TABLE XI

| Example 11 | Composition mg/capsule |
|---|---|
| Testosterone Undecanoate | 225 |
| Solubilizer (e.g. Castor Oil) | 350 |
| Dispersant (e.g. lauroglycol); | 180 |
| Solidifying agent (e.g. PEG 8000) | 45 |

TU- loading (wt %) of capsule fill = 28.1%

Examples 12-19

Testosterone Undecanoate Compositions

Testosterone undecanoate formulations of Examples 12 through 19 were prepared by using the components set forth in Table XII and by a method similar to that described under Example 1. Additionally, indicated amounts of the respective formulations were filled into hard gelatin capsules and the testosterone undecanoate release from capsules is measured using a USP Type-II apparatus at about 100 rpm in about 1000 mL of 8% w/w solution of Triton X100 in water, maintained at about 37° C. The results of the release testing are also shown in Table XII.

TABLE XII

| Capsule Components/Attributes | Composition mg/capsule | | | | | | | | |
|---|---|---|---|---|---|---|---|---|---|
| | Example 12 | Example 13 | Example 14 | Example 15 | Example 15A | Example 16 | Example 17 | Example 18 | Example 19 |
| Testosterone Undecanoate | 40 | 40 | 75 | 75 | 90 | 75 | 75 | 75 | 125 |
| Oleic Acid | 227 | — | — | — | — | — | — | — | — |
| Castor oil | — | 175 | — | — | — | 455 | — | — | — |
| Lauroglycol | — | 115 | — | — | — | — | — | — | — |
| Labrafil M2125CS | — | — | — | — | — | 80 | — | — | — |
| Maize oil glycerides (Maisine 35-1) | — | — | 455 | 455 | 315 | — | 316 | 316 | 515 |
| Polyoxyl 40 Hydrogenated Castor Oil, (Cremophor RH40) | — | — | 130 | 80 | 35 | — | 79 | 54 | 112 |

TABLE XII-continued

| Capsule Components/ Attributes | Composition mg/capsule | | | | | | | | |
|---|---|---|---|---|---|---|---|---|---|
| | Example 12 | Example 13 | Example 14 | Example 15 | Example 15A | Example 16 | Example 17 | Example 18 | Example 19 |
| Glyceryl distearate (Percirol ATO 5) | | — | — | 50 | 60 | — | — | 25 | |
| Polyethylene Glycol 8000, | | — | — | — | 48 | 30 | 30 | 48 | |
| Total mg per capsule (mg) | 267 | 330 | 660 | 660 | 500 | 660 | 500 | 500 | 800 |
| TU- loading (wt %) of capsule fill | 15% | 12% | 11.3% | 11.3% | 18% | 11.3% | 15% | 15% | 15.6% |
| TU released in 30 minutes (%) | ~100% | ~100% | ~100% | 30% | 30% | ~78% | 85% | 32% | 80% |
| Time for 75% TU release (minutes) | <120 | <120 | <120 | <120 | <120 | <120 | <120 | <120 | <120 |

Examples 20-25

Testosterone Undecanoate Compositions

Testosterone undecanoate formulations of Examples 20 through 25 were prepared by using the components set forth in Table XIII and by a method similar to that described under Example 1. Additionally, indicated amounts of the respective formulations were filled into hard gelatin capsules and the testosterone undecanoate release from capsules was tested in about 1000 mL of 8% w/w solution of Triton X100 in water, maintained at about 37° C., using a USP Type-II apparatus at about 100 rpm. The results of the release testing are also shown in Table XIII.

Examples 26-29

Testosterone undecanoate formulations of Examples 26 through 29 were prepared by using the components set forth in Table XIV and a method similar to that described under Example 1. Additionally, indicated amounts of the respective formulations were filled into hard gelatin capsules and the testosterone undecanoate released from capsules was tested in about 1000 mL of 8% w/w solution of Triton X100 in water, maintained at about 37° C., using a USP Type-II apparatus at about 100 rpm. The results of the release testing are also shown in Table XIV.

TABLE XIII

| Capsule Components/ Attributes | Composition mg/capsule | | | | | |
|---|---|---|---|---|---|---|
| | Example 20 | Example 21 | Example 22 | Example 23 | Example 24 | Example 25 |
| Testosterone Undecanoate (TU) | 200 | 200 | 240 | 240 | 240 | 240 |
| Maize oil glycerides (Maisine 35-1) | — | 490 | 464 | 464 | — | 304 |
| Coconut oil glycerides (Capmul MCM) | — | — | — | — | 400 | — |
| Alpha-tocopherol | 510 | — | — | 50 | — | 50 |
| Benzyl alcohol | — | — | — | — | 25 | 50 |
| Polyoxyl 40 Hydrogenated Castor Oil, | — | 25 | — | — | — | — |
| Polyoxyl 35 Castor Oil, | 45 | — | — | — | — | — |
| Polyethylene Glycol 8000, USP | 45 | 45 | — | 46 | 65 | 41 |
| Total Fill wt. per capsule (mg) | 800 | 760 | 704 | 800 | 730 | 685 |
| TU- loading (wt %) of capsule fill | 25 | 26.3 | 34.0 | 30.0 | 32.9 | 35.0 |
| TU released in 30 minutes | 43% | 62% | 38% | 32% | <75% | <75% |
| Time for 75% TU release (minutes) | <120 | <120 | <120 | <120 | <120 | <120 |

TABLE XIV

| Capsule Components/ Attributes | Composition mg/capsule | | | |
|---|---|---|---|---|
| | Example 26 | Example 27 | Example 28 | Example 29 |
| Testosterone Undecanoate | 250 | 250 | 250 | 250 |
| Maize oil glycerides (Maisine 35-1) | 486 | 937 | 410 | 939 |
| Polyoxyl 40 Hydrogenated Castor Oil (Cremophor RH40) | 25 | 213 | 69 | 144 |
| Glyceryl distearate (Percirol ATO 5) | — | — | 32 | 67 |
| Polyethylene Glycol 8000, | 39 | — | 39 | — |
| Total mg per capsule | 800 | 1400 | 800 | 1400 |
| TU- loading (wt % of capsule fill | 31.3 | 18 | 31.3 | 18 |
| TU released in 30 minutes | <75% | <75% | <75% | <75% |
| Time for 75% TU release (minutes) | <120 | <120 | <120 | <120 |

Note:
Examples 27 and 29 can optionally be disposed in a delayed release capsule Examples 30-35

Testosterone undecanoate formulations Examples 30 through 35 can be prepared by using the components set forth in Table XV and by a method similar to that described in Example 1. Additionally, indicated amounts of the respective formulations can be encapsulated in gelatin capsules and the testosterone undecanoate release from the capsules tested in about 1000 mL of 8% w/w solution of Triton X100 in water, maintained at about 37° C., using a USP Type-II apparatus at about 100 rpm. The results of the release testing are also shown in Table XV.

TABLE XV

| Capsule Components/ Attributes | Composition mg/capsule | | | | | |
|---|---|---|---|---|---|---|
| | Example 30 | Example 31 | Example 32 | Example 33 | Example 34 | Example 35 |
| Testosterone Undecanoate | 368 | 320 | 490 | 240 | 40 | 300 |
| Maize oil glycerides (Maisine 35-1) | 900 | 370 | 620 | 404 | — | — |
| Castor Oil | — | — | — | — | 175 | 276 |
| Lauroglycol | — | — | — | — | 115 | 184 |
| Tocopherol | — | — | 102 | — | — | — |
| Benzyl alcohol | — | — | 102 | — | — | — |
| Polyoxyl 40 Hydrogenated Castor Oil, | 46 | 25 | — | — | — | — |
| Polyethylene Glycol 8000, USP | 86 | 45 | 86 | 41 | — | — |
| TU- loading (wt %) of capsule fill | 26.3 | 36.3 | 35.0 | 35.0 | 12.0 | 39.5 |
| Total Fill wt. per capsule | 1400 | 760 | 1400 | 685 | 330 | 760 |
| TU released in 30 minutes | 62% | <62% | <75% | <75% | ~100% | <75% |
| Time for 75% TU release (minutes) | <120 | >120 | <120 | <120 | <120 | >120 |

Examples 30 through 35 demonstrate the importance of the choice of the solubilizers of the current invention and their levels to achieve greater testosterone undecanoate loading and yet maintain the solubilization of the testosterone undecanoate in the composition and/or the dosage form.

Examples 36 and 37

Testosterone Undecanoate Containing Compositions

The compositions of the current invention can be further adsorbed onto one or more substrate materials such as, for example, lactose, magnesium aluminosilicate, colloidal silicon dioxide, starch, microcrystalline cellulose, alkyl celluloses etc., whereby a free flowing powder/granule form is obtained which can be used as a granules, or disposed into capsule, or pressed into tablet. The amount of the substrate material can be from about 15% to about 40% of the weight of the composition. In one embodiment, the amount of the substrate material can be from about 20% to about 35% of the weight of the formed granule or powder. The method of making such adsorbed testosterone undecanoate compositions can include pouring the liquid compositions on the substrate material under and continuous mixing at room temperature or at about 50° C.-70° C., depending on the composition. After cooling, the adsorbed composition can be disposed into capsule or pressed into tablet. Table XVI illustrates examples of the freely flowable adsorbed solubilized testosterone undecanoate compositions.

TABLE XVI

| Components/Attributes | Composition (% w/w) | |
|---|---|---|
| | Example 36 | Example 37 |
| Testosterone Undecanoate | 16 | 16 |
| Maize oil glycerides (Maisine 35-1) | 50 | — |
| Castor Oil | — | 45 |

TABLE XVI-continued

| Components/Attributes | Composition (% w/w) | |
|---|---|---|
| | Example 36 | Example 37 |
| Sorbitan monolaurate (Span ® 20) | — | 5 |
| Tocopherol | 1 | — |
| Glycerylpalmito stearate | 5 | — |
| Polyoxyl 40 Hydrogenated Castor Oil, | 3 | — |
| Polyethylene Glycol 8000, USP | — | 4 |
| Magnesium aluminosilicate (Neusilin ® US2) | 25 | 30 |

Example 38

Stability of Testosterone Undecanoate Containing Compositions

A preliminary stability evaluation with respect to the change in potency and/or appearance of the potential primary degradation products was carried out with the compositions of Example 17 and Example 21, both filled in hard gelatin capsules at 200 mg/per capsule and 75 mg per capsules. The capsules were packed in HDPE bottles and staged for stability studies in the environmental chambers maintained at 25° C./60% RH. The primary degradation products were determined by a HPLC analysis method after about three months' storage and the results shown in Table XVII.

TABLE XVII

| TU composition | Degradant |
|---|---|
| Example 17 | 0.15% |
| Example 21 | 0.06% |

Examples 39, 39A, and 40 to 47

Testosterone Undecanoate Containing Compositions

Testosterone undecanoate-containing compositions (capsule fill material) were prepared by using the components set forth in Tables XVIII and XIX. It should be noted that Example 40 and 47 are expressed as wt % of Examples 17 and 12 respectively. The compositions are prepared by weighing all of the components, except the testosterone undecanoate, into a clean stainless steel container and mixed together at about 50° C. to about 70° C., using a stirrer. The testosterone undecanoate (TU) is added and stirred into the mixture of other components until the testosterone undecanoate dissolves. A predetermined quantity of the "capsule fill" was disposed into a capsule (for example, hard gelatin capsule) to get the required testosterone undecanoate dose per dosage unit. The capsules are allowed to cool at room temperature, banded (if required) and packaged in a HDPE bottle and tightly closed with an appropriate lid.

TABLE XVIII

| Capsule Components/Attributes | Example 39 | Example 39A | Example 40 | Example 41 | Example 42 |
|---|---|---|---|---|---|
| Testosterone Undecanoate, wt % | 14 | 14 | 15 | 18 | 18 |
| Monoglycerides (e.g. maize oil monoglycerides, Maisine 35-1), wt % | 64 | 75 | 63 | 68 | 68 |
| Hydrophilic surfactants (e.g. Cremophor RH40, Cremophor EL), wt % | 16 | 5 | 16 | 8 | 14 |
| Fatty acids (e.g. linoleic acid, Linolenic acid, Oleic Acid), wt % | — | — | — | — | — |
| Triglyceride (e.g. castor oil, maize oil, borage seed oil, laurogylcol, corn oil etc.), wt % | — | — | — | — | — |
| Lipophilic surfactant (e.g. propylene glycol monolaurate), wt % | — | — | — | — | — |
| Solidifying agent (e.g. polyethylene glycol 8000), wt % | 6 | 6 | 6 | 6 | — |
| % TU dissolved at RT | 70-75 | 85-92 | 65-70 | 50-55 | 55-60 |
| % TU undissolved fraction at RT | 25-30 | 8-15 | 30-35 | 45-50 | 40-45 |

*It is noted that the compositions can also include one or more components such as anti-oxidants (e.g. BHA, BHT, Ascorbyl palmitate, vitamin E or combinations), flavorings etc.

TABLE XIX

| Capsule Components/Attributes | Example 43 | Example 44 | Example 45 | Example 46 | Example 47 |
|---|---|---|---|---|---|
| Testosterone Undecanoate, wt % | 25 | 18 | 20 | 12 | 12 |
| Monoglycerides (e.g. maize oil monoglycerides, Maisine 35-1), wt % | 70 | — | — | — | — |
| Hydrophilic surfactants (e.g. Cremophor RH40, Cremophor EL), wt % | 5 | 17 | 16 | — | — |
| Fatty acids (e.g. linoleic acid, Linolenic acid, Oleic Acid), wt % | — | 53 | 52 | 88 | — |
| Triglyceride (e.g. castor oil, maize oil, borage seed oil, laurogylcol, corn oil etc.), wt % | — | 12 | 12 | — | 53 |
| Lipophilic surfactant (e.g. propylene glycol monolaurate), wt % | — | — | — | — | 35 |
| Solidifying agent (e.g. polyethylene glycol 8000), wt % | — | — | — | — | — |
| % TU dissolved at RT | 40-45 | 100 | 100 | 100 | 100 |
| % TU undissolved fraction at RT | 55-60 | 0 | 0 | 0 | 0 |

*It is noted that the compositions can also include one or more components such as anti-oxidants (e.g. BHA, BHT, Ascorbyl palmitate, vitamin E or combinations), flavorings etc.

The compositions of tables XVIII and XIX include descriptions of the amounts of testosterone undecanoate that is dissolved at room temperature (RT). The percent (%) of the undissolved testosterone undecanoate in the composition at RT can range from about 5 wt % to about 60 wt %. Examples 44 to 47 do not include a solidifying agent and that about 100 wt % of the testosterone undecanoate is dissolved in these composition. All Examples, except Examples 44 to 47, are free of ionizable fatty acids such as oleic acid.

Example 48

The clinical testing for the select inventive composition examples were conducted in a randomized study in human subjects including hypogonadal males having a pre-test screening serum testosterone concentrations less than 3 ng/mL (~10.5 nmol/L). The study compositions were administered orally with at least 240 mL of water about 30 minutes after starting a standardized meal (at least 30-35% fat) which was preceded by a fast of about 10 hours. The testing methodology allows for determining single dose pharmacokinetic profiles. Dose amounts as well as mean pharmacokinetic parameters from the testing are shown in the Table XX.

TABLE XX

| Attribute | Example 15A | Example 40 | Example 41 | Example 45 | Example 47 |
|---|---|---|---|---|---|
| Total daily TU dose administered, mg | 360-460 | 430-460 | 430-460 | 600-650 | 240 |
| Mean $C_{max}$ to mean $C_{ave}$ ratio | 1.54-2.69 | 1.54-2.69 | 1.54-2.69 | 1.93 | >2.84 |
| Dose-normalized $C_{max}$, $dL^{-1}$ | $3 \times 10^{-6}$ to $7 \times 10^{-6}$ | $3 \times 10^{-6}$ to $7 \times 10^{-6}$ | $3 \times 10^{-6}$ to $7 \times 10^{-6}$ | $3 \times 10^{-6}$ to $7 \times 10^{-6}$ | $1.6 \times 10^{-6}$ |

As can be seen from the data presented in Table XX, Examples 40, 41, and 45 provide a higher dose normalized $C_{max}$ and a lower $C_{max}$ to $C_{ave}$ ratio after single dose administration (one half of the daily dose) as compared to Example 47, which is a lower loading, fully dissolved composition.

Example 49

Examples 40, 41, 44, and 45 were clinically tested in a randomized study in human male subjects, including hypogonadal males having pre-test serum testosterone concentrations less than 3 ng/mL (~10.5 nmol/L). The example compositions were administered orally with at least 240 mL of water about 30 minutes after starting a standardized meal (at least 30-35% fat) which was preceded by a fast of about 10 hours. The testing methodology allows for determining single dose PK profiles. Dose amounts as well as mean pharmacokinetic parameters from the testing are shown in Table XXI.

TABLE XXI

| Attribute | Example 40 | Example 41 | Example 44 | Example 45 |
|---|---|---|---|---|
| Total daily TU dose administered, mg | 430-460 | 430-460 | 632 | 632 |
| Dose-normalized $C_{ave}$, $dL^{-1}$ | $>1.9 \times 10^{-6}$ | $>2.7 \times 10^{-6}$ | $\leq 1.63 \times 10^{-6}$ | $\leq 1.63 \times 10^{-6}$ |

As can be seen in Table XXI, the compositions of Example 40 and 41 provide a desirable higher dose normalized $C_{ave}$ (bioavailability) after single dose administration (one half of the daily dose) as compared to Examples 44 and 45. It is noteworthy that the testosterone undecanoate in Examples 44 and 45 is fully dissolved in the composition at room temperature. Further, each of Examples 44 and 45 contain oleic acid, an ionizable fatty acid, and each is devoid of solids (i.e. a solidifying agent and/or undissolved testosterone undecanoate).

Example 50

Based on test results from Examples 40, 41 and 45 pharmacokinetic (PK) performance parameters related to target pharmacokinetic criteria in a group of hypogonadal men with no dose titration (i.e. the maintenance dose is the same as the initial TU daily dose) were estimated. The data shown is based on normal patient distribution and a variability of about 50%, although similar results are expected if the variability changes up to an additional 15%. The simulated PK performance parameters allow for the $C_{ave}$ and $C_{max}$ to be measured on different days after day 84. Table XXII shows the estimated parameters for Examples 40, 41 and 45, including various daily dose quantities for the compositions and capsules Example 40.

TABLE XXII

| Attribute/ | Example 40A | Example 40B | Example 40C | Example 40D | Example 41 | Example 45 |
|---|---|---|---|---|---|---|
| Total daily TU dose, mg | 150 | 360-420 | 430 | 1000 | 340-400 | 632 |
| Target PK Criteria | Group PK Performance Results | | | | | |
| $C_{avg}$ in the range of 300-1100 ng/dL | <75% | >75% | <75% | <75% | >75% | <75% |
| $C_{max}$ is less than 1500 ng/dL | >85% | >85% | >85% | <85% | >85% | <85% |
| $C_{max}$ in the range between 1800 and 2500 ng/dL | <5% | <5% | <5% | >5% | <5% | >5% |
| $C_{max}$ greater than 2500 ng/dL | <1% | <1% | <1% | >1% | <1% | >1% |

Based on the results shown in Table XXII, it is evident that dosing based on Example 40-B and Example 41 provide PK performance criteria which may not require individualized titrations of the daily dose.

Example 51

Based on test results from Examples 40 and 45, pharmacokinetic (PK) performance parameters were estimated related to target PK criteria in a group of hypogonadal men using a dose titration metric of $C_{ave}$ with a single dose titration. The estimated data is based on normal patient distribution and a variability of about 50%. Similar results are expected if the variability in PK parameters and/or maintenance dose changes by up to 15% or the selection of another relevant dose-sensitive metric, such as $C_t$, $C_{max}$, $C_{min}$, or the like. The simulated PK performance parameters allow for the $C_{ave}$ and $C_{max}$ to be measured on different days after day 90. Table XXIII shows the estimated parameters for Examples 40 and 45, including various daily dose quantities for the compositions and capsules of Example 40.

TABLE XXIII

|  | Example | | | Example |
| --- | --- | --- | --- | --- |
|  | 40A | 40E | 40D | 45 |
| Total TU initial Daily Dose (IDD), mg | 150 | 360-460 | 1000 | 580-650 |
| Maintenance Daily Dose (% of IDD) | ±40 | ±40 | ±40 | ±40 |
| PK Performance Criteria | Group PK Performance Results | | | |
| $C_{avg}$ in the range of 300-1100 ng/dL | <75% | >75% | <75% | <75% |
| $C_{max}$ is less than 1500 ng/dL | >85% | >85% | <85% | <85% |
| $C_{max}$ in the range between 1800 and 2500 ng/dL | <5% | <5% | >5% | >5% |
| $C_{max}$ greater than 2500 ng/dL | <1% | <1% | >1% | >1% |

Based on the results shown in Table XXIII, it is evident that high loading testosterone undecanoate compositions, such as Example 40-E, meet target PK performance criteria with a single individualized titration of the daily dose into a maintenance dose in responders to the exogenous TU and who are in need of a dose change based on titration metric results.

Example 52

Based on test results from Examples 40 and 45, pharmacokinetic performance parameters were estimated related to target PK criteria in a group of hypogonadal men using a dose titration metric of $C_{ave}$ and two dose titrations. The estimated data is based on normal patient distribution and a variability of about 50%. Similar results are expected if the variability in PK parameters and/or maintenance dose changes by up to 15% or the selection of another relevant dose-sensitive metric, such as $C_t$, $C_{max}$, $C_{min}$, or the like. The simulated PK performance parameters allow for the $C_{ave}$ and $C_{max}$ to be measured on different days after day 90. Table XXIV shows the estimated parameters for Examples 40 and 45, including various daily dose quantities for the compositions and capsules Example 40.

TABLE XXIV

|  | Example | | | Example |
| --- | --- | --- | --- | --- |
|  | 40A | 40E | 40C | 45 |
| Total TU Initial Daily (IDD) | 150 | 360-460 | 1000 | 580-650 |
| Maintenance Daily Dose (% of IDD) | ±40 | ±40 | ±40 | ±40 |
| PK Performance Criteria | Group PK Performance Results | | | |
| $C_{avg}$ in the range of 300-1100 ng/dL | <75% | >75% | <75% | >75% |
| $C_{max}$ is less than 1500 ng/dL | >85% | >85% | <85% | >85% |
| $C_{max}$ in the range between 1800 and 2500 ng/dL | <5% | <5% | >5% | <5% |
| $C_{max}$ greater than 2500 ng/dL | <1% | <1% | >1% | >1% |

Based on the estimated values shown in Table XXIV, it is evident that high loading testosterone undecanoate compositions, such as Example 40-E, meet target PK performance criteria with a two individualized titration of the daily dose into a maintenance dose in responders to the exogenous TU and who are in need of a dose change based on titration metric results.

Example 53

Based on test results from Examples 40 41, 44 and 45, pharmacokinetic performance parameters were estimated related to target pharmacokinetic criteria in a group of hypogonadal men using a dose titration metric of $C_{ave}$ and three dose titrations. The estimated data is based on normal patient distribution and a variability of about 50%. Similar results are expected if the variability in PK parameters and/or maintenance dose changes by up to 15% or the selection of another relevant dose-sensitive metric, such as $C_t$, $C_{max}$, $C_{min}$, or the like. The simulated PK performance parameters allow for the $C_{ave}$ and $C_{max}$ to be measured on different days after day 90. Table XXV shows the estimated parameters for Examples 40, 41, 44 and 45, including various daily dose quantities for the compositions and capsules Example 40.

TABLE XXV

|  | Example | | | Example | Example | |
| --- | --- | --- | --- | --- | --- | --- |
|  | 40A | 40E | 40D | 41 | 44 | Example 45 |
| Total TU Initial Daily (IDD) dose | 120 | 360-460 | 1000 | 350-440 | 580-650 | 580-650 |
| Maintenance Daily Dose (% of IDD) | ±40 | ±40 | ±40 | ±40 | ±40 | ±40 |
| PK Performance Criteria | Group PK Performance Results | | | | | |
| $C_{avg}$ in the range of 300-1100 ng/dL | <75% | >75% | <75% | >75% | >75% | >75% |

TABLE XXV-continued

|  | Example | | | Example | Example | |
|---|---|---|---|---|---|---|
|  | 40A | 40E | 40D | 41 | 44 | Example 45 |
| $C_{max}$ is less than 1500 ng/dL | >85% | >85% | <85% | >85% | >85% | >85% |
| $C_{max}$ in the range between 1800 and 2500 ng/dL | <5% | <5% | >5% | <5% | <5% | <5% |
| $C_{max}$ greater than 2500 ng/dL | <1% | <1% | >1% | <1% | <1% | <1% |

Based on the results shown in Table XXV, it is evident that high loading testosterone undecanoate compositions, such as Examples 40-E, 41, 44, and 45 meet target PK performance criteria with a up to three individualized titrations of the daily dose into a subsequent maintenance doses in responders to the exogenous TU and who are in need of a dose changes based on titration metric results. As evident from the results of the Examples in Tables XXII to XXV, upon each subsequent titration, the compositions disclosed herein offer higher patient dose tolerance and increased chances of success to achieve serum testosterone in the eugonadal range.

Example 54

Clinical Practice Titration Metrics

Patient and physician-friendly clinical practice titrations metrics were derived from the titration node day PK measurements ($C_{ave}$) following steady state (>15 days) administration of the high loading testosterone undecanoate compositions disclosed herein. It should be noted that as the $C_{ave}$ and $C_{max}$ were observed to have a strong correlation, the $C_{max}$ data could also be used to arrive at a similar clinical practice titration metric. As noted above in the application, $C_t$ is the serum total testosterone concentration upon single testosterone administration, after "t" hours post-dose of a typical single daily dose of a BID daily dose regimen on the titration node day. Table XXVI shows a titration table based on the titration metric $C_t$ for various time points following administration.

TABLE XXVI

| Sampling Time "t"(hours post-dose) | "Up-titration" Ct limit (ng/ml) | "Down-titration" Ct limit (ng/ml) |
|---|---|---|
| t = 2 | 1.96 | 9.39 |
| t = 4 | 4.12 | 18.08 |

TABLE XXVI-continued

| Sampling Time "t"(hours post-dose) | "Up-titration" Ct limit (ng/ml) | "Down-titration" Ct limit (ng/ml) |
|---|---|---|
| t = 6 | 5.46 | 16.37 |
| t = 8 | 2.97 | 7.83 |
| t = 12 | 1.35 | 2.93 |

For example, those subjects in a group of hypogonadal men, whose C2 (i.e. Ct at t=2) is <1.96 ng/mL would have to be administered with a higher (for e.g. from about 125% to 155% of the dose prior to the titration) maintenance TU dose going forward ("up-titration") for effective testosterone therapy. Whereas those subjects in a group of hypogonadal men, whose C2 (i.e. Ct at t=2) is >9.39 ng/mL, would have to be administered with a lower (for example, from about 45 to 75% of the dose prior to the titration) maintenance TU dose going forward ("down-titration") for effective testosterone therapy. It should also be noted that the "t" can be within about 1 hour.

Example 55

Dosing Regimens for Effective Testosterone Therapy in Hypogonadal Males

Dosing regimens were prepared based on simulated data from observed steady state PK data in hypogonadal men assuming a normal patient distribution and with variability of about 50% and a dose titration metric of $C_{ave}$. Similar results can be expected if the variability in PK parameters changes by up to 15% using titration metric $C_t$ relationship given in Table-XXVI. Safety assessment can be done any day the $C_{max}$ is measured for a testosterone product (typically, 84 days from initial dosing). Similarly, efficacy assessments can be done any day the $C_{ave}$ is measured for a testosterone product (typically, 84 days from initial dosing). The regimens are prepared based on the understanding that the $C_{ave}$ and $C_{max}$ can be measured on different days.

TABLE XXVII

| Dosing Methodology | Oral Total TU Initial Daily Dose (IDD), mg | No. of TU Dose Titrations | Maintenance Daily Dose (as % change from IDD) | Metric for serum total T, (ng/mL) | $C_{ave}$ on efficacy assessment day, (ng/dL) | $C_{max}$ on safety assessment day, (ng/dL) |
|---|---|---|---|---|---|---|
| A | 350-650 | 3 | ±25-55% | Ct | >300 | <1500 |
| B | 580-650 | 2 | ±25-55% | Ct | >300 | <1500 |
| C | 360-480 | 1 | ±25-55% | Ct | >300 | <1500 |
| D | 350-420 | 0 | ±25-55% | Ct | >300 | <1500 |
| E | 650-900 | 3 | ±25-55% | Ct | >300 | >1500 |

Unlike the recommended imprecise oral TU dosing regimen for the commercially available product Andriol®, the dosing regimen methodology disclosed herein for subjects in need of dose adjustments (high or low responders, such as illustrated in Example dosing methods, A to D) includes appropriate initial daily dose, maintenance dose and titration metric result in effective testosterone therapy ($C_{ave}$>300 ng/dL) for optimal efficacy, while maintaining the $C_{max}$<1500 ng/dL in order to provide a better safety profile. It should be noted that dosing method E for a compositions of this invention would require more than three titrations which would generally be inconvenient, impractical, and may not allow for high levels of patient compliance.

It is understood that the above-described various types of compositions, dosage forms and/or modes of applications are only illustrative of preferred embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that variations including, but not limited to, variations in size, materials, shape, form, function and manner of operation, assembly and use may be made without departing from the principles and concepts set forth herein.

The invention claimed is:

1. A method for providing a serum concentration of testosterone within a steady state target serum testosterone concentration $C_{ave}$ range for a hypogonadal male subject having testosterone deficiency, comprising the steps of,
    1) orally administering to the male subject twice a day with a meal an initial regimen including a daily dose of a testosterone undecanoate-containing composition, wherein the testosterone undecanoate comprises about 14 wt % to about 35 wt % of the testosterone undecanoate-containing composition and wherein the daily dose provides about 360 mg to about 480 mg of testosterone undecanoate to the male subject;
    2) determining a dose titration metric based on a measurement of serum testosterone concentration for the male subject on at least one titration node day within the initial regimen said measurement of serum testosterone concentration made from 1 to 8 hours after single dose administration of said testosterone undecanoate-containing composition at steady state; and
    3) orally administering to the male subject twice a day with a meal a maintenance regimen including a daily dose of a testosterone undecanoate-containing composition, wherein the testosterone undecanoate-containing composition comprises about 14 wt % to about 35 wt % of the testosterone undecanoate-containing composition and wherein the maintenance regimen provides a daily dose of testosterone undecanoate within ±40% of the amount of testosterone undecanoate of the initial regimen daily dose to the subject based on the titration metric determined on the at least one titration node day of the initial regimen sufficient to provide a serum testosterone plasma concentration within the target range
    wherein the testosterone undecanoate-containing composition provides upon single dose administration a ratio of serum testosterone $C_{max}$ to $C_{ave}$ of 2.7 or less or provides a dose-normalized serum testosterone $C_{ave}$ of about 1.9× $10^{-6}$ dL$^{-1}$ or higher.

2. The method of claim 1, further comprising the steps of:
    4) determining a dose titration metric based on a measurement of serum testosterone concentration for the male subject on at least one titration node day within the maintenance regimen;
    5) orally administering to the male subject a second maintenance regimen including a daily dose of a testosterone undecanoate-containing composition, wherein the testosterone undecanoate-containing composition comprises about 14 wt % to about 35 wt % of the testosterone undecanoate-containing composition and wherein the second maintenance regimen provides a daily dose of testosterone undecanoate to the subject based on the titration metric determined on the at least one titration node day of the maintenance regimen sufficient to provide a serum testosterone plasma concentration within the target range; and optionally
    6) repeating steps 4 and 5, if needed.

3. The method of claim 1, wherein the daily dose administered in the initial regimen is the same dosage amount as the daily dose administered in the maintenance regimen.

4. The method of claim 1, wherein the titration node day is any single day from day 15 to day 84 following the start of the initial regimen.

5. The method of claim 1, wherein the testosterone undecanoate dose titration can be such that:
    i) if at time (t) of 1 to less than 3 hours following administration the serum testosterone concentration is less than 2.0 ng/mL there is an increase in dose and if the serum testosterone concentration is more than 9.4 ng/mL there is a decrease in dose; or
    ii) if at time (t) of 3 to less than 8 hours following administration the serum testosterone concentration is less than 4.1 ng/mL there is an increase in dose and if the serum testosterone concentration is more than 18.1 ng/mL there is a decrease in dose.

6. The method of claim 1, wherein the target serum testosterone Cave range is about 300 ng/dL to 1100 ng/dL and is achieved on or after day 84 following the start of the initial regimen.

7. The method of claim 1, wherein the daily dose of testosterone undecanoate for the initial regimen is more than the daily dose of testosterone undecanoate for the maintenance regimen.

8. The method of claim 1, wherein the method provides a serum testosterone Cave in the range of 300 ng/dL to 1100 ng/dL in 75% or more of hypogonadal males after 84 days from the start of the initial regimen based on a minimum group size of 24 hypogonadal males.

9. The method of claim 1, wherein the method provides a serum testosterone Cmax of 1500 ng/dL or less in at least 85% of hypogonadal males after 84 days from the start of the initial regimen based on a minimum group size of 24 hypogonadal males.

10. The method of claim 1, wherein the method provides a serum testosterone Cmax in the range of 1800 ng/dL to 2500 ng/dL in about 5% or less of hypogonadal males after 84 days from the start of the initial regimen based on a minimum group size of 24 hypogonadal males.

11. The method of claim 1, wherein the method provides a serum testosterone Cmax of 2500 ng/dL in about 1% or less of hypogonadal males after 84 days from the start of the initial regimen based on a minimum group size of 24 hypogonadal males.

12. The method of claim 1, wherein testosterone undecanoate comprises about 14 wt % to about 18 wt % of the testosterone undecanoate-containing composition.

13. The method of claim 1, wherein said hypogonadal male subject has a baseline serum testosterone concentration of less than 300 ng/dL.

14. The method of claim 1, wherein the method provides a steady state serum testosterone Cave of from 350 ng/dL to 800 ng/dL.

15. The method of claim 1, wherein the initial regimen daily dose of testosterone undecanoate is from 360 mg to 460 mg.

16. The method of claim 1, wherein the initial regimen daily dose of testosterone undecanoate is from 430 mg to 460 mg.

17. The method of claim 1, wherein said meal has from about 10 g to about 50 g fat.

18. The method of claim 1, wherein the method provides a mean serum testosterone Cave in range of 350-800 ng/dL in a group of hypogonadal subjects having 24 hypogonadal males.

19. The method of claim 15, wherein the method provides a mean serum testosterone steady state Cave in range of 400-600 ng/dL in a group of hypogonadal subjects having 24 hypogonadal males.

20. A method for providing a serum concentration of testosterone within a target serum testosterone concentration $C_{ave}$ range for a hypogonadal male subject having testosterone deficiency, comprising the steps of,
   1) orally administering to said hypogonadal male subject an initial regimen including a daily dose of a testosterone undecanoate-containing composition having from about 350 mg to about 650 mg of testosterone undecanoate; and
   2) orally administering to the male subject a first maintenance regimen including a daily dose of a testosterone undecanoate-containing composition that is within ±40% of the amount of testosterone undecanoate of the initial regimen daily dose wherein the daily dose of the maintenance regimen is determined by the serum concentration of testosterone at time t (Ct) at steady state during the initial regimen wherein Ct is correlated to the Cmax and Cave values of a population of hypogonadal men receiving said initial regimen to determine the maintenance regimen daily dose said serum testosterone concentration determined from 1 to 8 hours after single dose administration of said testosterone undecanoate-containing composition at steady state.

21. The method of claim 20 wherein $C_t$ is determined at a time of from 0 to 2 hours, 2 to 4 hours, or 4 to 6 hours, after administration of a single dose of said testosterone undecanote-containing composition.

22. The method of claim 20 further comprising administering a second maintenance dose regimen having a daily dose of testosterone undecanoate that is within ±40% of the amount of testosterone undecanoate of the first maintenance regimen daily dose.

23. The method of claim 22 wherein the second maintenance regimen daily dose is determined by correlating said hypogonadal male subject's Ct to Cmax and Cave values of a population of hypogonadal men receiving said initial regimen to determine the second maintenance regimen daily dose.

24. The method of claim 20 wherein the initial regimen daily dose is from about 430 mg to about 460 mg testosterone undecanoate.

25. The method of claim 1 having a total of three different daily doses of testosterone undecanoate for the initial and maintenance regimens.

26. The method of claim 20 wherein said method (i) provides a serum testosterone Cave of 300 ng/dL to 1100 ng/dL in at least 75% of a group of hypogonadal male subjects and (ii) provides a) a serum testosterone Cmax of less than 1500 ng/dL in at least 85% of the subjects in the group; b) a serum testosterone Cmax of about 1800 ng/dL to about 2500 ng/dL in 5% or less of the subjects in the group; or c) a serum testosterone Cmax greater than 2500 ng/dL in about 1% or less of the subjects in the group.

27. The method of claim 20, wherein the daily dose of testosterone undecanoate for the maintenance regimen is lower than the daily dose of testosterone undecanoate for the initial regimen.

* * * * *